US008771679B2

(12) United States Patent
Ostermeier et al.

(10) Patent No.: US 8,771,679 B2
(45) Date of Patent: Jul. 8, 2014

(54) PRODRUG ACTIVATION IN CANCER CELLS USING MOLECULAR SWITCHES

(75) Inventors: Marc Alan Ostermeier, Baltimore, MD (US); Chapman M. Wright, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 154 days.

(21) Appl. No.: 13/059,014

(22) PCT Filed: Aug. 13, 2009

(86) PCT No.: PCT/US2009/004653
§ 371 (c)(1),
(2), (4) Date: Feb. 14, 2011

(87) PCT Pub. No.: WO2010/019257
PCT Pub. Date: Feb. 18, 2010

(65) Prior Publication Data
US 2011/0135620 A1    Jun. 9, 2011

Related U.S. Application Data

(60) Provisional application No. 61/088,388, filed on Aug. 13, 2008.

(51) Int. Cl.
*A61K 38/43* (2006.01)

(52) U.S. Cl.
USPC ...................................................... 424/94.1

(58) Field of Classification Search
None
See application file for complete search history.

(56) References Cited

U.S. PATENT DOCUMENTS

| 6,339,070 | B1 | 1/2002 | Emery et al. |
| 7,393,524 | B2 | 7/2008 | Maitland |
| 2002/0182229 | A1 | 12/2002 | Brown et al. |
| 2005/0158324 | A1 | 7/2005 | Emtage |
| 2006/0177423 | A1 | 8/2006 | Both et al. |
| 2009/0005266 | A1 | 1/2009 | Ostermeier et al. |

FOREIGN PATENT DOCUMENTS

WO    9109134 A1    6/1991

OTHER PUBLICATIONS

Freedman et al., Structural basis for recruitment of CBP/p300 by hypoxia-inducible factor-1 alpha, PNAS, Apr. 16, 2002, vol. 99, No. 8, 5367-5372.*
Guntas et al., Directed Evolution of Protein Switches and their application to the creation of ligand-binding proteins, PNAS, Aug. 9, 2005, vol. 102, No. 32, pp. 11224-11229.*

* cited by examiner

*Primary Examiner* — Suzanne M Noakes
*Assistant Examiner* — Stephen Chong
(74) *Attorney, Agent, or Firm* — Edwards Wildman Palmer LLP; Peter F. Corless

(57) ABSTRACT

The present invention features a novel protein engineering strategy by combining the domains of two independent proteins into a molecular switch. The invention features polypeptides comprising a prodrug activating enzyme and a protein that binds a cancer specific marker, polynucleotides encoding the polypeptides, and molecular switches for converting a prodrug into a toxin, comprising the polypeptides. The invention also features methods for converting a prodrug into a toxin, methods for treating cancer, and methods for making the molecular switches, as well as kits.

4 Claims, 8 Drawing Sheets

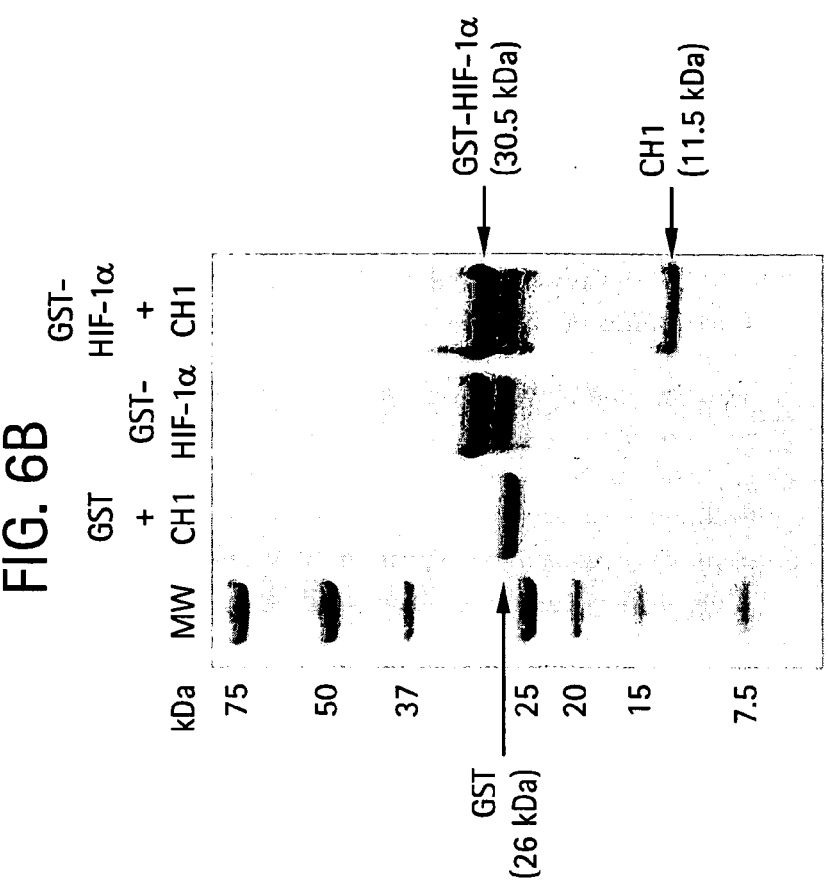
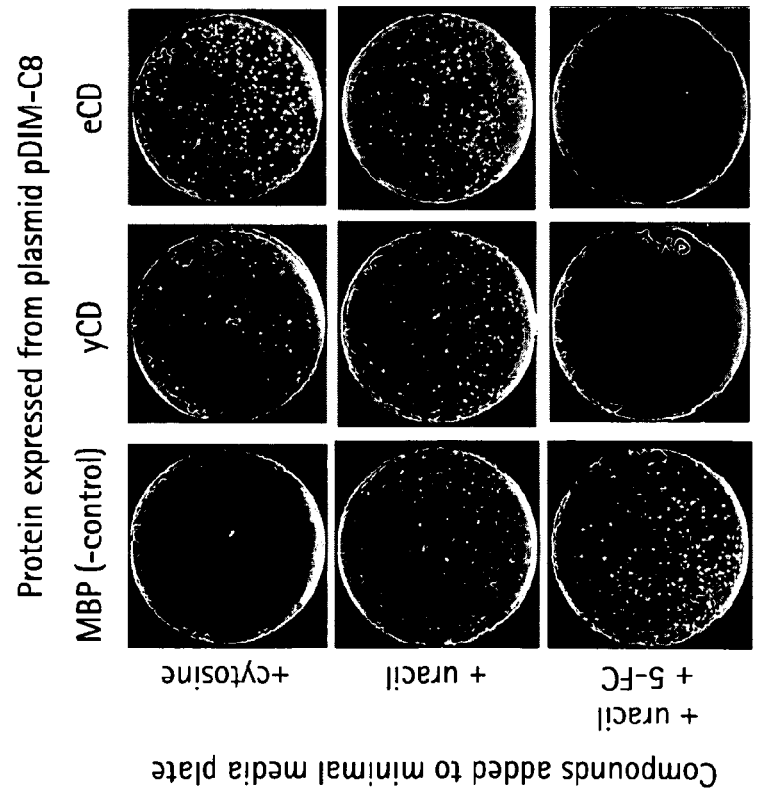

PRODRUG ACTIVATION IN CANCER CELLS USING MOLECULAR SWITCHES

CROSS-REFERENCE TO RELATED APPLICATIONS

This application is a 35 U.S.C. §371 U.S. national entry of International Application PCT/US2009/004653 (WO 2010/019257) having an International filing date of Aug. 13, 2009 which claims the benefit of U.S. Provisional Application No. 61/088,388, which was filed Aug. 13, 2008, the entire contents of which applications are incorporated herein by reference.

BACKGROUND OF THE INVENTION

The complexity of biological systems stems to a large extent from the high degree of interactions amongst their constituent components. As such, the cell is often described as a complex circuit consisting of an interacting network of molecules. Fusion proteins that function as molecular switches and serve to couple cellular functions are key components of this network. A switch recognizes an input signal (e.g. ligand concentration, pH, covalent modification) and, as a result, its output signal (e.g. enzyme activity, ligand affinity, oligomeric state) is modified. Examples of natural switches include allosteric enzymes which couple effector levels to enzymatic activity and ligand-dependent transcription factors that couple ligand concentration to gene expression. The ability to create novel switches or to modify existing switches by coupling previously uncoupled protein functions would enable the creation of selective protein therapeutics that are able to "sense" the cellular state and carryout the desired function conditionally depending on that state. In addition, the ability to create protein switches has tremendous practical potential for developing novel molecular sensors, medical diagnostics and as a tool for elucidating molecular and cellular functions. Additionally, such switches are an addition to the synthetic biologist's toolbox for creating programmable cells for biotechnological and bioengineering applications because they directly link the protein's specific activity to the cellular state.

There is recognition that there is great potential to design fusion proteins that act as molecular switches to modulate or report on biological functions for a variety of applications including biosensors, modulators of gene transcription and cell signaling pathways, and novel biomaterials. Despite its great potential, however, molecular switch technology has not been extensively exploited, in part due to technical challenges in engineering effective molecular switches. Most existing strategies for engineering switches involve the reprogramming of existing switches, the engineering of control over protein interactions the alleviating of the effects of deleterious mutations by the binding of small molecules, or the modulation of protein folding. In general, existing approaches to creating protein molecular switches include: control of oligomerization or proximity using chemical inducers of dimerization (CID); chemical rescue; fusion of the target protein to a steroid binding domain (SBD); coupling of proteins to non-biological materials or metal nanocrystals, and domain insertion.

Gene-directed enzyme prodrug therapy (GDEPT; also known as "suicide gene therapy") is an emerging gene therapy strategy against cancer. In GDEPT, the gene encoding an enzyme, which can activate the prodrug, is delivered to cancer cells. This step is followed by the systemic administration of a prodrug. This prodrug is converted to the toxic drug by the enzyme. To the extent that the enzyme is produced only in cancer cells, the toxic drug will be produced only in cancer cells.

Current approaches to GDEPT attempt to achieve specificity in two ways. The specificity of the prodrug activation has to rely on either targeted delivery of the gene to the desired cancer cells (transductional targeting) or the ability to limit gene expression to the targeted cells (transcriptional targeting). Transductional targeting suffers from the difficulty in creating gene delivery vehicles that are both efficient and specific (since, in general, efficiency is sacrificed for specificity). Although systemic virus administration is likely to be more effective, all clinical GDEPT studies to date have utilized local administration of the viral vectors at or near the tumor site because of transductional targeting limitations. The extent to which normal tissues are transduced with the suicide gene limits the dose of prodrug that can be administers and the effectiveness of the treatment. Transcriptional targeting is a more recent approach that attempts to circumvent this problem either by using tumor-selective promoters to drive expression of one or more viral genes that regulate viral replication (hence tumor cells will have more copies of the suicide gene and thus produced more the prodrug-converting enzyme) or by using tumor-selective promoters to drive expression of the suicide gene. However, viral replication increases the risk of insertional mutagenesis and oncogenesis. The majority of successful studies using tumor-selective promoters have been preclinical animal model studies with uncertain relevance to human cancer. The success of this approach will depend on the promoter strength in tumor cells and the lack of transcription in normal cells. It is not clear at present whether the difference between the two will be sufficient for effective selectivity.

There remains a need in the art for better cancer therapeutics, and in particular, better methods to more efficiently treat cancer cells while reducing the side-effects associated with these treatments.

SUMMARY OF THE INVENTION

As described below, the present invention features a novel protein engineering strategy by combining the domains of two independent proteins into a single molecular switch. The present invention uses the cancer cell's biology to turn on prodrug activation and, accordingly, to turn on treatment, and it uses a protein switch as a therapeutic agent. Activation of the prodrug is specific to the cancer cell due to this molecular switch.

Accordingly, in a first aspect, the invention features a polypeptide comprising a prodrug activating enzyme and a protein that interacts with a cancer specific marker.

In one embodiment, the prodrug activating enzyme is selected from the group consisting of: cytosine deaminase, thymidine kinase, nitroreductase, carboxypeptidase A, cytochrome P450, beta-glucosidase and beta-lactamase. In a related embodiment, the prodrug activating enzyme is cytosine deaminase (CD).

In another embodiment, the cancer specific marker is selected from the group consisting of: HIF-1a, beta-catenin, p53, prostate specific antigen (PSA), HER-2/neu, breast cancer antigen 1 and 2 (BRCA1/BRCA2), alpha-fetoprotein (AFP), carcinoembryonic antigen (CEA), epidermal growth factor receptor (EGFR), mammalian target of rapamycin (mTOR) and tumor protein D52 (TPD52). In a further related embodiment, the cancer specific marker is HIF-1a.

In another embodiment of the present invention, the protein that interacts with a cancer specific marker is selected from the group consisting of: p300, APC, $TCF_4$, RAD51, mLST8/GBL and MAL2. In a further related embodiment, the protein that interacts with a cancer specific marker is p300. In another related embodiment, a CH1 domain from p300 interacts with the cancer specific marker.

In another embodiment, the cancer specific marker is HIF-1a.

In another aspect, the invention features a polypeptide encoding a molecular switch comprising a cytosine deaminase and a CH1 domain from p300.

In one embodiment, the polypeptide comprises the amino acid sequence of SEQ ID NO: 1. In another embodiment, the polypeptide comprises the amino acid sequence of SEQ ID NO: 2.

In still another embodiment, the cytosine deaminase is from yeast or *E. coli*.

In another further embodiment, the sequence corresponding to cytosine deaminase contains one or more alterations. In a related embodiment, the alterations in the CD domain are stabilizing mutations. In another related embodiment, the stabilizing mutation is an A23LN1081/1140L stabilizing mutation in yeast CD domain.

In another embodiment, the invention features a polynucleotide encoding a polypeptide of any one of the above aspects.

In one embodiment, the polypeptide comprises the nucleic acid sequence of SEQ ID NO: 3. In another embodiment, the polypeptide comprises the nucleic acid sequence of SEQ ID NO: 4.

In another embodiment, the invention features a vector comprising a polynucleotide of any one of the above aspects, suitable for expression in a cell.

In one embodiment, the vector is a viral vector. In a related embodiment, the vector is a non-integrative viral vector.

In another embodiment, the invention features a cell transformed with the vector of the aspects described herein.

In one embodiment, the cell is an *E. coli* cell. In another embodiment, the cell is a mammalian cell.

In another embodiment, the invention features a method of producing one or more cells expressing a polypeptide comprising a prodrug activating enzyme and a protein that binds a cancer specific marker, comprising introducing into the cells the vector of the aspects described herein.

In another embodiment, the invention features a polypeptide of any one of the aspects described herein, wherein in the presence of the cancer specific marker, the protein that binds a cancer specific marker activates the prodrug activating enzyme.

In another embodiment, the invention features a molecular switch for converting a prodrug into a toxin, comprising the polypeptide of the aspects as described herein, wherein the protein that binds a cancer specific marker activates the prodrug activating enzyme.

In one embodiment, the molecular switch further comprises a compound that binds to the protein that binds a cancer specific marker and activates the prodrug activating enzyme. In a related embodiment, the prodrug activating enzyme is selected from the group consisting of: cytosine deaminase, thymidine kinase, nitroreductase, carboxypeptidase A, cytochrome P450, beta-glucosidase and beta-lactamase. In another particular embodiment, the prodrug activating enzyme is cytosine deaminase (CD).

In one embodiment, the cancer specific marker is selected from the group consisting of: HIF-1a, beta-catenin, p53, prostate specific antigen (PSA), HER-2/neu, breast cancer antigen 1 and 2 (BRCA1/BRCA2), alpha-fetoprotein (AFP), carcinoembryonic antigen (CEA), epidermal growth factor receptor (EGFR), mammalian target of rapamycin (mTOR) and tumor protein D52 (TPD52). In a particular embodiment, the cancer specific marker is HIF-1a.

In one embodiment, the protein that interacts with a cancer specific marker is selected from the group consisting of: p300, APC, TCF4, RAD51, mLST8/GBL and MAL2. In a particular embodiment, the protein that interacts with a cancer specific marker is p300.

In another embodiment, a CH1 domain from the human p300 protein interacts with the cancer specific marker.

In another aspect, the invention features a molecular switch for converting a prodrug into a toxin, comprising a cytosine deaminase and a CH1 domain.

In one embodiment, the molecular switch corresponds to the amino acid sequence of SEQ ID NO: 1. In one embodiment, the molecular switch corresponds to the amino acid sequence of SEQ ID NO: 2.

In another aspect, the invention features a method to convert a prodrug into a toxin in a cell that expresses a cancer specific marker comprising expressing a polypeptide comprising a prodrug activating enzyme and a protein that binds a cancer specific marker in a cell; and treating the cells with a prodrug, wherein the protein that binds the cancer specific marker binds the marker in a cell that expresses the marker and activates the prodrug activating enzyme, thereby converting the prodrug into a toxin.

In another aspect, the invention features a method of treating cancer in a subject comprising contacting one or more cells in a subject with a polypeptide comprising a prodrug activating enzyme and a protein that binds a cancer specific marker; and treating the subject with a prodrug, wherein the protein that binds the cancer specific marker binds the marker in a cell that expresses the marker and activates the prodrug activating enzyme, thereby converting the prodrug into a toxin, thereby treating cancer in a subject.

In one embodiment, the cancer is selected from the group consisting of: lung, breast, prostate and colon cancer.

In another embodiment, the prodrug activating enzyme is selected from the group consisting of: cytosine deaminase, thymidine kinase, nitroreductase, carboxypeptidase A, cytochrome P450, beta-glucosidase and beta-lactamase. In a related embodiment, the prodrug activating enzyme is cytosine deaminase (CD).

In another embodiment of the above aspects, the cancer specific marker is selected from the group consisting of: HIF-1a, beta-catenin, p53, prostate specific antigen (PSA), HER-2/neu, breast cancer antigen 1 and 2 (BRCA1/BRCA2), alpha-fetoprotein (AFP), carcinoembryonic antigen (CEA), epidermal growth factor receptor (EGFR), mammalian target of rapamycin (mTOR) and tumor protein D52 (TPD52). In a further embodiment, the cancer specific marker is HIF-1a.

In another embodiment of the above aspects, the protein that interacts with a cancer specific marker is selected from the group consisting of: p300, APC, TCF4, RAD51, mLST8/GBL and MAL2. In a further particular embodiment, the protein that interacts with a cancer specific marker is p300. In another further embodiment, a CH1 domain from the human p300 protein interacts with the cancer specific marker.

In another aspect, the invention features a method to convert a prodrug into a toxin in a cell that expresses a cancer specific marker, wherein the marker is HIF-1a, comprising expressing a polypeptide comprising a cytosine deaminase (CD) and a CH1 domain in a cell; and treating the cells with a prodrug, wherein the CH1 domain activates cytosine deaminase in cells that express HIF-1a, thereby converting the prodrug into a toxin.

In one embodiment, the prodrug is selected from the group consisting of: fluorocytosine (5-FC), ganciclovir, 5-(Aziridin-1-yl)-2,4-dinitrobenzamide (CB 1954), methotrexate-alanine, ifosfamide, anygdalin, cephalosporin-derivatized prodrugs. In a further embodiment, the prodrug is 5-FC.

In another aspect, the invention features a method to convert 5-FC into 5-fluorouracil (5-FU) in a cell that expresses a cancer specific marker, wherein the marker is HIF-1a, comprising expressing a polypeptide comprising a cytosine deaminase (CD) and a CH1 domain in a cell, and treating the cells with a prodrug, wherein the CH1 domain activates cytosine deaminase in cells that express HIF-1a, thereby converting 5-FC into 5-FU.

In another aspect, the invention features a method of treating cancer in a subject comprising contacting one or more cells in a subject with a polypeptide comprising a cytosine deaminase (CD) and a CH1 domain; and treating the subject with 5-FC, wherein the CH1 domain activates cytosine deaminase in cells that express HIF-1a, thereby converting 5-FC into 5-FU into a toxin, thereby converting the prodrug into a toxin, and treating cancer in a subject.

In another aspect, the invention features a method of making a molecular switch comprising providing a DNA library comprising one or more nucleotide sequences coding for the CH1 domain and one or more nucleotide sequences coding for the CD domain, performing circular permutation of the CH1 domain, randomly inserting the CH1 domain into the CD domain, thereby making a molecular switch.

In another aspect, the invention features a method of making a molecular switch comprising providing a DNA library comprising one or more nucleotide sequences coding for the CH1 domain and one or more nucleotide sequences coding for the CD domain, randomly inserting the CH1 domain into the CD domain, thereby making a molecular switch.

In one embodiment, the inserting is at an insertion site.

In one embodiment, the CH1 domain comprises a linker.

In one embodiment, the linker is selected from the group consisting of: GGS, GGGGS.

In one embodiment, the linker is selected from the group consisting of: GSGGG, (GSGGG)$_2$ and (GSGGG)$_3$.

In one embodiment of the above aspects, fusions in which cellular enzyme activity is modulated by the ligand of the sensing domain are identified through genetic selections.

In another embodiment, the genetic selection is a selection for HIF-1 a-activation of deaminase activity.

In another aspect, the invention features a kit comprising the polypeptide of any one of the aspects as described herein, and instructions for use.

Other features and advantages of the invention will be apparent from the detailed description, and from the claims.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 6 (A and B) is two panels where (A) shows positive and negative selection for CD activity in GIA39 cells on minimal media and (B) shows production and co-purification of GST-HIF-1a and the CH1 domain of p300. The soluble fractions of lysates of cells expressing the indicated proteins were passed over a glutathione column, eluted with glutathione and run on an SDS-PAGE gel (stained with coomassie blue; shown).

DETAILED DESCRIPTION OF THE INVENTION

Figure 1:
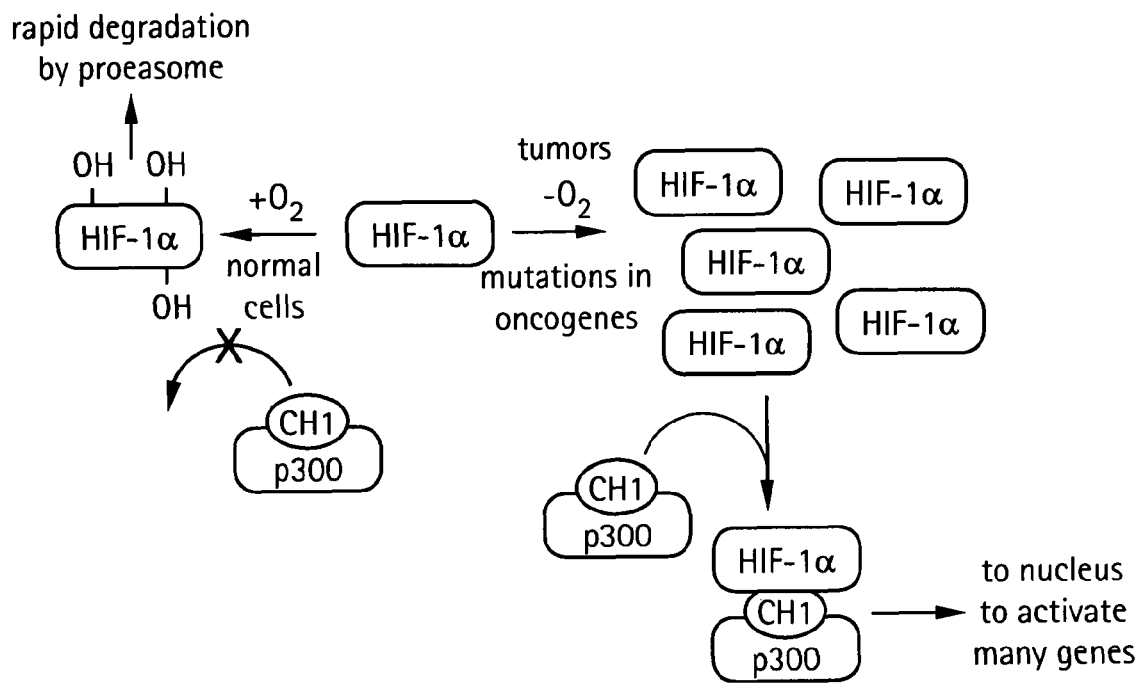
FIG. 1 is a schematic of HIF-1 hypoxia response.

The present invention describes a novel protein engineering strategy by combining the domains of two independent proteins into a single hybrid protein. The present invention described a novel approach to GDEPT using switches that uses gene delivery to deliver the therapeutic switch gene that can activate the prodrug. The present approach is novel as it utilizes a targeting strategy distinct from transductional and transcription targeting. The present approach does not necessarily require specific delivery to target cells or activation of the gene in target cells because the catalytic activity that activates the prodrug is preferably regulated at the enzyme level and is preferably activated only in the target cells. Accordingly, the present invention allows methods to efficiently deliver genes to the target cells to be used (methods that may lack cell-specificity), since expression of the therapeutic protein in non-target cells will not result in prodrug activation since the cells lack the signal to activate the enzyme.

I. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless otherwise specified, "a" or "an" means "one or more".

Unless specifically stated or obvious from context, as used herein, the term "or" is understood to be inclusive.

As used herein, the term "activated" is meant to refer to a molecule or portion thereof which performs an activity, such as catalyzing a substrate, emitting light, transferring electrons, transporting or localizing a molecule; changing conformation; binding to a molecule, etc.

As used herein, the term "alteration" is meant to refer to an addition, substitution or deletion of one or more amino acids in a polypeptide. In preferred embodiments, the alteration is a stabilizing mutation. In certain preferred embodiments, the alteration does not substantially alter the state of the polypeptide.

The terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, the term "cancer specific marker" is meant to refer to any protein or polynucleotide having an alteration in expression level or activity that is associated with cancer or a neoplasia. In particular embodiments, a "cancer specific marker" refers to a protein that is expressed only in cancer cells and that, when recognized and ligated to a protein that is part of a molecular switch and that binds a cancer specific marker, selectively activates the molecular switch. In preferred embodiments, the cancer specific marker refers to, but is not limited to, HIF-1a.

As used herein, the term "coupled" is meant to refer to a state which is dependent on another state such that a measurable change in the other state is observed.

As used herein, the term "circularly permuted" is meant to refer to a nucleic acid or protein sequence in which the primary sequence differs from the original non-circularly permuted sequence in a specific way. For a nucleic acid, the circularly permuted sequence differs in that a continuous sequence that was on the 3' end in the non-circularly permuted sequence is attached to the 5' end in the circularly permuted sequence. The circularly permuted nucleic acid may or may not have a linker sequence between the original 5' and 3' ends. For a protein, the circularly permuted sequence differs in that a continuous sequence that was on the C-terminus in the non-circularly permuted sequence is attached to the N-terminus in the circularly permuted sequence. The circularly permuted protein may or may not have a linker sequence between the original N- and C-termini. A circularly permuted sequence can be conceptualized as joining the ends of an original, linear non-circularly permuted sequence to form a cyclized sequence, and converting the cyclized sequence back to a linear sequence by breaking the bonds at a new location. Although a circularly permuted sequence can be created in this manner, as used herein, the term "circularly permuted sequence" can also include the same sequence created by other means not involving a cyclized intermediate. "Randomly circularly permuted" as used herein refers to a sequence in which a circularly permuted sequence is created in which the site of circular permutation is determined by a random, semi-random or stochastic process.

As used herein, the term "host cell" is meant to refer to any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

As used herein, the term "inactivated" is meant to refer to a molecule or portion thereof which is, at least temporarily, unable to perform an activity or exist in a particular state (e.g., bind to a molecule, change conformation, etc.).

The term "an insertion sequence" as used herein is meant to refer to a polymeric sequence which is contained within another polymeric sequence (e.g., an "acceptor sequence") and which conditionally alters the state of the other polymeric sequence. An insertion sequence or acceptor sequence can comprise a polypeptide sequence, nucleic acid sequence (DNA sequence, aptamer sequence, RNA sequence, ribozyme sequence, hybrid sequence, modified or analogous nucleic acid sequence, etc.), carbohydrate sequence, and the like. Nucleic acid and amino acid sequences for use as acceptor and insertion sequences in the invention can be naturally occurring sequences, engineered sequences (for example, modified natural sequences), or sequences designed de novo.

As used herein, "at an insertion site" of a nucleic acid molecule refers to from about 1 to 21 nucleotides immediately flanking the insertion site.

As used herein, the term "molecular switch" refers to a molecule which generates a change in state in response to a signal. In one aspect, a molecular switch is capable of switching from at least one state to at least one other state in response to the signal. Preferably, when a portion of the molecule responds to the signal, the portion becomes activated (i.e., turns "ON") or inactivated (i.e., turns "OFF"). In response to this change in state, the state of another portion of the fusion molecule will change (e.g., turn ON or OFF). In one aspect, a switch molecule turns ON one portion of the molecule when another portion is turned OFF. In another aspect, the switch turns ON one portion of the molecule, when the other portion is turned ON. In still another aspect, the switch molecule turns OFF one portion of the molecule when the other portion is turned ON. In a further aspect, the switch molecule turns OFF when the other portion is turned OFF. In a particular embodiment of the present invention, the protein switch comprises a polypeptide comprising a prodrug activating enzyme and a protein that binds a cancer specific marker, where the protein that binds a cancer specific marker activates the prodrug activating enzyme.

In some aspects of the invention, a switch exists in more than two states, i.e., not simply ON or OFF. For example, a portion of the fusion molecule may display a series of states (e.g., responding to different levels of signal), while another portion of the fusion molecule responds at each state, with a change in one or more states. A molecular switch also can comprise a plurality of fusion molecules responsive to a signal and which mediate a function by changing the state of at least a portion of the molecule (preferably, in response to a change in state of another portion of the molecule). While the states of individual fusion molecules in the population may be ON or OFF, the aggregate population of molecules may not be able to mediate the function unless a threshold number of molecules switch states. Thus, the "state" of the population of molecules may be somewhere in between ON or OFF depending on the number of molecules which have switched states. In one aspect, a molecular switch comprises a heterogeneous population of fusion molecules comprising members which switch states upon exposure to different levels of signal. In other aspects of the invention, however, the state of a single molecule may be somewhere in between ON or OFF. For example, a molecule may comprise a given level of activity, ability to bind, etc., in one state which is switched to another given level of activity, ability to bind, etc., in another state (i.e., an activity, ability to bind, etc., measurably higher or lower than the activity, ability to bind, etc., observed in the previous state).

As used herein, the term "prodrug" is meant to refer to any compound that undergoes biotransformation before exhibiting its pharmacological effects. In certain examples, the prodrug is fluorocytosine (5-FC). A prodrug activating enzyme converts a prodrug into its active form.

As used herein, a "state" refers to a condition of being. For example, a "state of a molecule" or a "state of a portion of a molecule" can be a conformation, binding affinity, or activity (e.g., including, but not limited to, ability to catalyze a substrate; ability to emit light, transfer electrons, transport or localize a molecule, modulate transcription, translation, replication, supercoiling, and the like).

As used herein, the term "subject" is intended to include vertebrates, preferably a mammal. Mammals include, but are not limited to, humans.

As used herein, the terms "treat," treating," "treatment," and the like are meant to refer to reducing or ameliorating a disorder and/or symptoms associated therewith. It will be appreciated that, although not precluded, treating a disorder or condition does not require that the disorder, condition or symptoms associated therewith be completely eliminated. In preferred embodiments of the invention, the disease is cancer.

As used herein, a "vector" is meant to refer to a nucleic acid molecule, for example, a plasmid, cosmid, or bacteriophage, that is capable of replication in a host cell. In one embodiment, a vector is an expression vector that is a nucleic acid construct, generated recombinantly or synthetically, bearing a series of specified nucleic acid elements that enable transcription of a nucleic acid molecule in a host cell. Typically, expression is placed under the control of certain regulatory elements, including constitutive or inducible promoters, tissue-preferred regulatory elements, and enhancers. As used herein, a "viral vector" refers to a virus or viral particle that comprises a polynucleotide to be delivered into a host cell, either in vivo, ex vivo or in vitro. In preferred embodiments, the vector is a non-integrative viral vector.

Each patent, patent application, or reference cited herein is hereby incorporated by reference as if each were incorporated by reference individually.

Molecular Switches

In one aspect, the present invention provides molecular switches comprising a polypeptide comprising a prodrug activating enzyme and a protein that binds a cancer specific marker.

In exemplary embodiments, in the presence of the cancer specific marker, the protein that binds a cancer specific marker activates the prodrug activating enzyme.

In certain embodiments, the protein that binds the cancer specific marker is selected from adenomatous polyposis coli (APC), transcription factor 4 (TCF4), RAD51, mLST8/GβL, and MAL2. In further related embodiments, APC and TCF4 bind the cancer marker beta-catenin.

According to the present invention, any number or different cancer markers can be envisioned. For example, the cancer marker may be a tumor suppressor gene. A "tumor-suppressor gene", as used herein, is a gene that when mutated to functionally alter or inactivate the gene product results in an increased susceptibility to genomic instability and cancer. Mutation of a tumor-suppressor gene often results in a loss-of-function such that the gene product does not induce genomic instability alone, but instead allows for cell growth and division to occur without the proper controls. Tumor-suppressor genes, as used herein, have a number of functions within the cell including DNA-repair, cell cycle checkpoints, transcriptional regulation, cell adhesion and motility, signal transduction, transport, metabolism including RNA metabolism, and intracellular trafficking. (The DNA-repair genes and other genes involved in genome maintenance are sometimes considered as a distinct subset, but herein we will include them among the tumor-suppressor genes.) Many transcription factors are tumor-suppressor genes or oncogenes, and thus mutations or aberrant regulation of them are associated with cancer. For example, Li-Fraumeni syndrome is caused by mutations in the tumor-suppressor p53. Other transcription factors associated with cancer and/or believed to be tumor-suppressor genes include, but are not limited to SMAD2 and SMAD4.

There are also many tumor-suppressor genes for which specific functions have not been assigned. Some tumor-suppressor genes are associated with specific cancers, whereas others are not.

In certain preferred embodiments, the cancer marker is selected from, but not limited to, BRCA1, BRCA2, MLH1, MSH2, MSH6, EPHA3, EPHA4, APHB2, INI1, AXIN1, AXIN2, MLL3, EP300, NF1, TP53, APC, VHL, SMAD2, SMAD4, KEAP1, CDKN2A, RB1, MEN, NF2/SCH, PTCH, TGFBR1, TGFBR2, ACVR1B, AVCR2, MRE11, MAP2K4, LKB1/STK11ATM, ATR, FANCD2, FANCA, FANCB, FANCC, FANCD1, FANCE, FANCF, FANCG, FANCL, FANCM, FAAP100, FLNB, TMPRSS6, RAPH1 1.4 PKHD1, CNTN4, MYH1, COL11A1, PCDHB15, ADAMTSL3, CHL1, SPTAN1, DNAH9, CMYA1, OBSCN, HAPLN1, DBN1, OBSCN, MACF1, ADAMTS18, MGC33407, TECTA, COL7A1, SYNE2, MMP2, MAP2, ADAM12, MAGEE1, NRCAM, TTLL3, GSN, CDH10, COL19A1, EVL, CDH2O, SULF2, SEMA5B, ADAM29, BGN, CNTN6, ITGA9, CSMD3, ICAM5, THBS3, ADAMTSI5, VEPH1, PFC, PRPF4B, APC, PTPRD, SBNO1, GAB1, CENTG1, KRAS, MCP, DNASE1L3, ARHGEF4, MAP3K6, RAP1GA1, NALP8, APC2, GUCY1A2, PTPRU, EGFL6, RGL1, STARD8, EPHB6, CD109, AMFR, PPM1E, PTPN14, PHIP, CENTB1, PKDREJ, IRTA2, GNAS, GPNMB, CNNM4, RASGRF2, RET, INHBE, ALS2CL, MTMR3, P2RY14, FLJ10458 L. RASAL2, LGR6, CHD5, ZFP64, TP53, ZNF442, FLJ13479, CIC, ZNF569, SMAD3, SIX4, KEAP1, EHMT1, MLL3, EYA4, KIAA0934, HOXA3, ZFYVE26, TBX22, PKNOX1, LRRFIP1, TCF1, BCL11A, MKRN3, GLI1, HDAC4, ZNF318, TCF7L2, RFX2, $MYOD_1$, HIST1H1B, ZCSL3, NCOA6, RUNX1T1, ATP8B1, ABCB8, ABCB10, ABCA1, C6orf29, CUBN, KPNA5, SCNN1B, SLC29A1, GRIN2D, ABCA3, NUP133, SCN3B, HDLBP, SLC9A2, P2RX7, NUP214, SLC6A3, KCNQ5, ACADM, NCB50R, PHACS, UQCRC2, PRPS1. ASL, XDH, ACSL5, CYP1A 1, GALNT5, GALNS, OTOF, PLEKHA8, KTN1, SYNE1, PRKD1, LRBA, LOC283849, GGA1, SEC8L1, LRP2, AEGP, SORL1, SDBCAG84, C14orf155, RNU31P2, KIAA0427, SFRS6, SP110, C22orfl9, DDX10, FLJ40869, SERPINB1, FBXW7, K6IRS3, UHRF2, CD248, MRE11A, LMO7, ERCC6, KIAA1632, KIAA0999, C10orf137, KIAA1409, MGC24047, LOC157697, and C15orf2.

In certain preferred embodiments, the cancer marker is selected from the group consisting of: beta-catenin, p53, prostate specific antigen (PSA), HER-2/neu, breast cancer antigen 1 and 2 (BRCA1/BRCA2), alpha-fetoprotein (AFP), carcinoembryonic antigen (CEA), epidermal growth factor receptor (EGFR), mammalian target of rapamycin (mTOR), tumor protein D52 (TPD52).

In still other further embodiments, RAD51 binds the cancer marker breast cancer antigen 1 and 2 (BRCA1/BRCA2). In other further embodiments, mLST8/GβL binds the cancer marker mammalian target of rapamycin (mTOR). In still other embodiments, mal, T-cell differentiation protein 2 (MAL2) binds the cancer marker tumor protein D53 (TPD52).

In particular embodiments, the present invention provides molecular switches polypeptide encoding a gene switch comprising a cytosine deaminase and a CH1 domain. Preferably, molecular switches of the present invention can be used for converting a prodrug into a toxin, wherein the protein that binds a cancer specific marker activates the prodrug activating enzyme.

US Application No. 20090005266, incorporated by reference in its entirety herein, describes molecular switches with altered ligand recognition and binding, and methods of making these molecules involving circular permutation of nucleic acid or amino acid sequences.

In preferred embodiments, the present invention provides a modulatable fusion molecule which comprises an insertion sequence and an acceptor sequence which contains the insertion sequence. Preferably, the insertion sequence and acceptor sequence are polymeric molecules, e.g., such as polypeptides or nucleic acids.

In certain preferred embodiments of the present invention, the prodrug activating enzyme is an acceptor sequence and a protein that binds a cancer specific marker is an insertion sequence. In particular, the CH1 domain can function as the insertion sequence, and the CD domain is the acceptor sequence.

The size of the insertion in the fusion protein will vary depending on the size of insertion sequence required to confer a particular state on the insertion sequence without significantly disrupting the ability of the acceptor molecule into which it is inserted to change state. Preferably, the effect of the insertion is to couple the change in state of the acceptor molecule to a change in state of the insertion molecule, or vice versa.

Preferably, the protein that binds a cancer specific marker activates the prodrug activating enzyme.

Generally, for polypeptide insertions, the size of the insertion sequence can range from about two amino acids to at least about 1000, for example at least about 900, 800, 700, 600, 500, 400, 300, 200, 100, or fewer amino acids. In one aspect, the insertion comprises a domain sequence with a known characterized activity (e.g., a portion of a protein in which bioactivity resides); however, in other aspects, the insertion sequence comprises sequences up to an entire protein sequence.

Generally, there are no constraints on the size or type of acceptor sequence which can be used. Suitable polypeptides for acceptor molecules can be identified using domain assignment algorithms such as are known in the art (e.g., such as the PUU, DETECTIVE, DOMAK, and DomainParser, programs). For example, a consensus approach may be used as described in Jones, et al., (1998). Information also can be obtained from a number of molecular modeling databases such as the web-based NIH Molecular Modeling Homepage, or the 3Dee Database described by Dengler, et al., 2001, Proteins 42(3): 332-44. However, the most important criterion for selecting a sequence is its function, e.g., the desired state parameters of the fusion molecule.

However, in a further aspect, no pre-screening is done and an acceptor sequence is selected simply on the basis of a desired activity. The power of the methods according to the invention is that they rely on combinatorial screening to identify any, and preferably all, combinations of insertions that produce a desired coupling in states of acceptor and insertion molecules.

More preferably, both the insertion sequence and acceptor sequence are capable of existing in at least two states and the state of the insertion sequence is coupled to the state of the acceptor sequence upon fusion, such that a change in state in either the insertion sequence or acceptor sequence will result in a change in state of the respective other portion of the fusion. As discussed, a "state"" can be a conformation; binding affinity; ability or latent ability to catalyze a substrate; ability or latent ability to emit light; ability or latent ability to transfer electrons; ability or latent ability to withstand degradation (e.g., by a protease or nuclease); ability or latent ability to modulate transcription; ability or latent ability to modulate translation; ability or latent ability to modulate replication; ability or latent ability to initiate or mediate recombination or supercoiling; or otherwise perform a function; and the like.

Preferably, the change in state is triggered by a signal to which the fusion molecule is exposed, e.g., such as the presence, absence, or amount of a marker, e.g. a cancer specific marker expressed by a cell. Other signals include, but are not limited to a small molecule, ligand, metabolite, ion, organelle, cell membrane, cell, organism (e.g., such as a pathogen), temperature change, pressure change, and the like, to which the fusion molecule binds, or a change in a condition, such as pH, or a change in the chemical, optical, electrical, or magnetic environment of the fusion molecule.

In particular embodiments, in the presence of the cancer specific marker, the protein that binds a cancer specific marker activates the prodrug activating enzyme.

For example, the method can be applied such that when a cell expresses a cancer specific marker as described herein, the protein in the switch binds the cancer specific marker activates the prodrug activating enzyme in that cell, and the prodrug is converted to a toxic form.

In certain examples, the activating enzyme is selected from, but not limited to thymidine kinase, nitroreductase, carboxypeptidase A, cytochrome P450, beta-glucosidase, and beta-lactamase.

In preferred embodiments, thymidine kinase activates the prodrug ganciclovir to the active agent ganciclovir triphosphate.

In other preferred embodiments, nitroreductase activates the prodrug 5-(Aziridin-1-yl)-2,4-dinitrobenzamide (CB 1954) via its 4-hydroxylamine derivative to a potent bifunctional alkylating agent.

In other preferred embodiments, carboxypeptidase A activates methotrexate-alanine to the active agent methotrexate.

In other preferred embodiments, cytochrome P450 activates ifosfamide to its active agent ifosfamide mustard.

In other preferred embodiments, beta-glucosidase activates amygdalin to its active agent cyanide.

In other preferred embodiments, beta-lactamase activates cephalosporin-derivatized prodrugs to active agents.

In particular preferred embodiments of the present invention, the protein switch is activated in cancer cells by HIF1-a and then the prodrug (5FC) is converted into the anticancer drug (5FU). The protein switches will not be activated in normal cells because of the very low levels of HIF1-a and the prodrug will remain nontoxic.

In one aspect, a fusion molecule functions as an ON/OFF switch in response to a signal (e.g., changing from one state to another). For example, when an insertion sequence or acceptor sequence of the fusion molecule binds to a ligand, the respective other half of the fusion may change state (e.g., change conformation, bind to a molecule, release a molecule to which it is bound, catalyze a substrate or stop catalyzing a substrate, emit light or stop emitting light, transfer electrons or stop transferring electrons, activate or inhibit transcription, translation, replication, etc.).

Some fusion molecules according to the invention also can be used to generate graded responses. In this scenario, a fusion molecule can switch from a series of states (e.g., more than two different types of conformations, levels of activity, degrees of binding, levels of light transmission, electron transfer, transcription, translation, replication, etc.). Preferably, the difference in state is one which can be distinguished readily from other states (e.g., there is a significant measurable difference between one state and any other state, as determined using assays appropriate for measuring that state).

More generally, a molecular switch can generate a measurable change in state in response to a signal. For example, a molecular switch can comprise a plurality of fusion molecules each responsive to a signal and for mediating a function in response to a change in state of at least a portion of the molecule. As above, preferably, this change of state occurs in response to a change in the state of another portion of the molecule.

While the states of individual fusion molecules in the population may be ON or OFF, the aggregate population of molecules may not be able to mediate the function unless a threshold number of molecules switch states. Thus, the "state" of the population of molecules may be somewhere in between ON or OFF, depending on the number of molecules which have switched states. This provides an ability to more precisely tune a molecular response to a signal by selecting for molecules which respond to a range of signals and modifying the population of fusion molecules to provide selected numbers of fusion molecules, providing an aggregate switch which can respond to a narrow range or wider range of signal as desired. Thus, in one aspect, a heterogeneous population of fusion molecules is provided comprising members which respond to different levels or ranges of signals. Individual fusion molecules also may exist in states intermediate between ON or OFF; e.g., having a given level of activity, ability to bind to a molecule in one state and a measurably higher or lower level of activity, ability to bind, etc., in a different state.

Accordingly, the present invention features a polypeptide comprising a prodrug activating enzyme and a protein that binds a cancer specific marker.

In one embodiment, the prodrug activating enzyme is a cytosine deaminase (CD).

Cytosine deaminase (CD) is an enzyme that is able to convert the relatively harmless 5-fluorocytosine (5-FC) prodrug into the toxic 5-fluorouracil (5-FU). Accordingly, cancer cells that overexpress HIF-1a will activate the protein switch to convert 5-FC into 5-FU, thereby killing the cancer cells. This therapeutic protein could have the potential to be used in a treatment method that is analogous to GDEPT, but will have superior killing efficiency with reduced side-effects because the selectivity of our method arises at the molecular level.

The cytosine deaminase may be from yeast or *E. coli*. For example, an *E. coli* cytosine deaminase is represented in certain exemplary embodiments by NCBI Reference Sequence: NP_414871.1 (SEQ ID NO: 5): A yeast cytosine deaminase is represented in certain exemplary embodiments by GenBank Accession No. AAB67713.1 (SEQ ID NO: 6):

```
                                                                    SEQ ID NO: 5
  1 msnnalqtii narlpgeegl wqihlqdgki saidaqsgvm pitensldae qglvippfve 61 phihldttqt agqpnwnqsg tlfegierwa erkallthdd vkqrawqtlk wqiangiqhv 121 rthvdvsdat ltalkamlev kqevapwidl qivafpqegi lsypngeall eealrlgadv 181 vgaiphfeft reygveslhk tfalaqkydr lidvhcdeid deqsrfvetv aalahhegmg 241 arvtashtta mhsyngayts rlfrllkmsg infvanplvn ihlqgrfdty pkrrgitrvk 301 emlesginvc fghddvfdpw yplgtanmlq vlhmglhvcq lmgygqindg lnlithhsar 361 tlnlqdygia agnsanliil paengfdalr rqvpvrysvr ggkviastqp aqttvyleqp 421 eaidykr
```

SEQ ID NO: 6

```
  1 mvtggmaskw dqkgmdiaye eaalgykegg vpiggclinn kdgsvlgrgh nmrfqkgsat
 61 lhgeistlen cgrlegkvyk dttlyttlsp cdmctgaiim ygiprcvvge nvnfkskgek
121 ylqtrghevv vvdderckki mkqfiderpq dwfedige
```

In certain preferred embodiments, the sequence corresponding to cytosine deaminase contains one or more alterations. Preferably, the alterations in the CD domain are stabilizing mutations. An exemplary mutation is an A23L/V108I/I140L stabilizing mutation in yeast CD domain.

In another embodiment, the cancer specific marker is HIF-1a.

Hypoxia-inducible factor-1 (HIF1) is a transcription factor found in mammalian cells cultured under reduced oxygen tension that plays an essential role in cellular and systemic homeostatic responses to hypoxia. HIF1 is a heterodimer composed of an alpha subunit and a beta subunit. The beta subunit has been identified as the aryl hydrocarbon receptor nuclear translocator (ARNT). This gene encodes the alpha subunit of HIF-1. Overexpression of a natural antisense transcript (aHIF) of this gene has been shown to be associated with nonpapillary renal carcinomas. Two alternative transcripts encoding different isoforms have been identified.

*Homo sapiens* HIF-1a, variant 1, is represented by NCBI Reference Sequence NM_001530.3 shown below (SEQ ID NO: 7) and the corresponding amino acid sequence NCBI Reference Sequence NP_001521.1 (SEQ ID NO: 8):

SEQ ID NO: 7

```
   1 gcgcgcgccg gcctgggcag gcgagcgggc gcgctcccgc ccctctccc ctcccgcgc
  61 gcccgagcgc gcctccgccc ttgcccgccc cctgacgctg cctcagctcc tcagtgcaca
 121 gtgctgcctc gtctgagggg acaggaggat caccctcttc gtcgcttcgg ccagtgtgtc
 181 gggctgggcc ctgacaagcc acctgaggag aggctcggag ccgggcccgg accccggcga
 241 ttgccgcccg cttctctcta gtctcacgag gggtttcccg cctcgcaccc ccacctctgg
 301 acttgccttt ccttctcttc tccgcgtgtg gagggagcca gcgcttaggc cggagcgagc
 361 ctggggccg cccgccgtga agacatcgcg gggaccgatt caccatggag ggcgccggcg
 421 gcgcgaacga caagaaaaag ataagttctg aacgtcgaaa agaaaagtct cgagatgcag
 481 ccagatctcg gcgaagtaaa gaatctgaag ttttttatga gcttgctcat cagttgccac
 541 ttccacataa tgtgagttcg catcttgata aggcctctgt gatgaggctt accatcagct
 601 atttgcgtgt gaggaaactt ctggatgctg gtgatttgga tattgaagat gacatgaaag
 661 cacagatgaa ttgcttttat ttgaaagcct tggatggttt tgttatggtt ctcacagatg
 721 atggtgacat gatttacatt tctgataatg tgaacaaata catgggatta actcagtttg
 781 aactaactgg acacagtgtg tttgatttta ctcatccatg tgaccatgag gaaatgagag
 841 aaatgcttac acacagaaat ggccttgtga aaagggtaa agaacaaaac acacagcgaa
 901 gcttttttct cagaatgaag tgtacccctaa ctagccgagg aagaactatg aacataaagt
 961 ctgcaacatg gaaggtattg cactgcacag gccacattca cgtatatgat accaacagta
1021 accaacctca gtgtgggtat aagaaaccac ctatgacctg cttggtgctg atttgtgaac
1081 ccattcctca cccatcaaat attgaaattc ctttagatag caagactttc ctcagtcgac
1141 acagcctgga tatgaaattt tcttattgtg atgaaagaat taccgaattg atgggatatg
1201 agccagaaga acttttaggc cgctcaattt atgaatatta tcatgctttg gactctgatc
1261 atctgaccaa aactcatcat gatatgttta ctaaaggaca agtcaccaca ggacagtaca
1321 ggatgcttgc caaaagaggt ggatatgtct gggttgaaac tcaagcaact gtcatatata
1381 acaccaagaa ttctcaacca cagtgcattg tatgtgtgaa ttacgttgtg agtggtatta
1441 ttcagcacga cttgattttc tcccttcaac aaacagaatg tgtccttaaa ccggttgaat
1501 cttcagatat gaaaatgact cagctattca ccaaagttga atcagaagat acaagtagcc
1561 tctttgacaa acttaagaag gaacctgatg ctttaacttt gctggcccca gccgctggag
1621 acacaatcat atctttagat tttggcagca acgacacaga aactgatgac cagcaacttg
```

-continued

```
1681 aggaagtacc attatataat gatgtaatgc tccoctcacc caacgaaaaa ttacagaata
1741 taaatttggc aatgtctcca ttacccaccg ctgaaacgcc aaagccactt cgaagtagtg
1801 ctgaccctgc actcaatcaa gaagttgcat taaaattaga accaaatcca gagtcactgg
1861 aactttcttt taccatgccc cagattcagg atcagacacc tagtccttcc gatggaagca
1921 ctagacaaag ttcacctgag cctaatagtc ccagtgaata ttgtttttat gtggatagtg
1981 atatggtcaa tgaattcaag ttggaattgg tagaaaaact ttttgctgaa gacacagaag
2041 caaagaaccc attttctact caggacacag atttagactt ggagatgtta gctccctata
2101 tcccaatgga tgatgacttc cagttacgtt ccttcgatca gttgtcacca ttagaaagca
2161 gttccgcaag ccctgaaagc gcaagtcctc aaagcacagt tacagtattc cagcagactc
2221 aaatacaaga acctactgct aatgccacca ctaccactgc caccactgat gaattaaaaa
2281 cagtgacaaa agaccgtatg gaagacatta aaatattgat tgcatctcca tctcctaccc
2341 acatacataa agaaactact agtgccacat catcaccata tagagatact caaagtcgga
2401 cagcctcacc aaacagagca ggaaaaggag tcatagaaca gacagaaaaa tctcatccaa
2461 gaagccctaa cgtgttatct gtcgctttga gtcaaagaac tacagttcct gaggaagaac
2521 taaatccaaa gatactagct ttgcagaatg ctcagagaaa gcgaaaaatg gaacatgatg
2581 gttcactttt tcaagcagta ggaattggaa cattattaca gcagccagac gatcatgcag
2641 ctactacatc actttcttgg aaacgtgtaa aaggatgcaa atctagtgaa cagaatggaa
2701 tggagcaaaa gacaattatt ttaatacccc tgatttagc atgtagactg ctggggcaat
2761 caatggatga agtggatta ccacagctga ccagttatga ttgtgaagtt aatgctccta
2821 tacaaggcag cagaaaccta ctgcagggtg aagaattact cagagctttg gatcaagtta
2881 actgagcttt ttcttaattt cattccttt tttggacact ggtggctcat tacctaaagc
2941 agtctattta tatttctac atctaatttt agaagcctgg ctacaatact gcacaaactt
3001 ggttagttca attttgatcc cctttctact taatttacat taatgctctt ttttagtatg
3061 ttctttaatg ctggatcaca gacagctcat tttctcagtt ttttggtatt taaaccattg
3121 cattgcagta gcatcatttt aaaaaatgca cctttttatt tatttatttt tggctaggga
3181 gtttatccct ttttcgaatt atttttaaga agatgccaat ataattttg taagaaggca
3241 gtaacctttc atcatgatca taggcagttg aaaaattttt acacctttt tttcacattt
3301 tacataaata ataatgcttt gccagcagta cgtggtagcc acaattgcac aatatatttt
3361 cttaaaaaat accagcagtt actcatggaa tatattctgc gtttataaaa ctagttttta
3421 agaagaaatt ttttttggcc tatgaaattg ttaaacctgg aacatgacat tgttaatcat
3481 ataataatga ttcttaaatg ctgtatggtt tattatttaa atgggtaaag ccatttacat
3541 aatatagaaa gatatgcata tatctagaag gtatgtggca tttatttgga taaaattctc
3601 aattcagaga atcatctga tgtttctata gtcactttgc cagctcaaaa gaaaacaata
3661 ccctatgtag ttgtggaagt ttatgctaat attgtgtaac tgatattaaa cctaaatgtt
3721 ctgcctaccc tgttggtata aagatatttt gagcagactg taaacaagaa aaaaaaaatc
3781 atgcattctt agcaaaattg cctagtatgt taatttgctc aaaatacaat gtttgatttt
3841 atgcactttg tcgctattaa catcctttt ttcatgtaga tttcaataat tgagtaattt
3901 tagaagcatt attttaggaa tatatagttg tcacagtaaa tatcttgttt tttctatgta
3961 cattgtacaa attttcatt ccttttgctc tttgtggttg gatctaacac taactgtatt
4021 gttttgttac atcaaataaa catcttctgt ggaccaggca aaaaaaaaaa aaaaaaaaa
4081 aa
```

```
                                                                    SEQ ID NO: 8
  1 megaggandk kkisserrke ksrdaarsrr skesevfyel ahqlplphnv sshldkasvm 61 rltisylrvr klldagdldi eddmkaqmnc fylkaldgfv mvltddgdmi yisdnvnkym 121 gltqfeltgh svfdfthpcd heemremlth rnglvkkgke qntqrsiflr mkctltsrgr 181 tmniksatwk vlhctghihv ydtnsnqpqc gykkppmtcl vlicepiphp snieipldsk 241 tflsrhsldm kfsycderit elmgyepeel lgrsiyeyyh aldsdhltkt hhdmftkgqv 301 ttgqyrmlak rggyvwvetq atviyntkns qpqcivcvny vvsgiiqhdl ifslqqtecv 361 lkpvessdmk mtqlftkves edtsslfdkl kkepdaltll apaagdtiis ldfgsndtet 421 ddqqleevpl yndvmlpspn eklqninlam splptaetpk plrssadpal nqevalklep 481 npeslelsft mpqiqdqtps psdgstrqss pepnspseyc fyvdsdmvne fklelveklf 541 aedteaknpf stqdtdldle mlapyipmdd dfqlrsfdql splesssasp esaspqstvt 601 vfqqtqiqep tanattttat tdelktvtkd rmedikilia spspthihke ttsatsspyr 661 dtqsrtaspn ragkgvieqt ekshprspnv lsvalsqrtt vpeeelnpki lalqnaqrkr 721 kmehdgslfq avgigtllqq pddhaattsl swkrvkgcks seqngmeqkt iilipsdlac 781 rllgqsmdes glpqltsydc evnapiqgsr nllqgeellr aldqvn
```

In other exemplary embodiments, the protein that binds a cancer specific marker is a CH1 domain, preferably from the human p300 protein.

In certain embodiments of the invention, the molecular switch comprises a polypeptide comprising the amino acid sequence of SEQ ID NO: 1. IN SEQ ID NO: 1, shown below, the segment origination from CH1 is shown in bold and underlined. The corresponding nucleic acid sequence is shown as SEQ ID NO: 3.

```
                                                    SEQ ID NO: 1
MVTGGMAS GDPEKRKLIQQQLVLLLHAHKCQRREQANGEVRQCNLPHC
RTMKNVLNHMTHCQSGKSCQVAHCASSRQIISHWKNCTRHDCPVCLPL
KNAGGS KWDQKGMDIAYEEALLGYKEGGVPIGGCLINNKDGSVLGRGH
NMRFQKGSATLHGEISTLENCGRLEGKVYKDTTLYTTLSPCDMCTGAI
IMYGIPRCVIGENVNFKSKGEKYLQTRGHEVVVVDDERCKKLMKQFID
ERPQDWFEDIGE
```

```
                                                    SEQ ID NO: 3
ATGGTGACAGGGGGAATGGCAAGCGGCGATCCGGAAAAACGTAAACTG
ATCCAGCAGCAGCTGGTGCTGCTGCTGCATGCTCACAAATGTCAGCGT
CGTGAACAGGCAAACGGCGAAGTACGTCAGTGCAACCTGCCGCACTGC
CGTACAATGAAAAATGTACTGAACCACATGACCCACTGCCAGAGCGGT
AAAAGCTGCCAGGTAGCTCACTGCGCATCTTCTCGCCAGATTATCTCT
CACTGGAAAAACTGCACCCGTCACGATTGCCCGGTTTGCTTGCCGCTC
AAGAACGCTGGTGGCTCGAAGTGGGATCAGAAGGGTATGGACATTGCC
TATGAGGAGGCGCTCTTAGGTTACAAAGAGGGTGGTGTTCCTATTGGC
GGATGTCTTATCAATAACAAAGACGGAAGTGTTCTCGGTCGTGGTCAC
AACATGAGATTTCAAAAGGGATCCGCCACACTACATGGTGAGATCTCC
ACTTTGGAAAACTGTGGGAGATTAGAGGGCAAAGTGTACAAAGATACC
ACTTTGTATACGACGCTGTCTCCATGCGACATGTGTACAGGTGCCATC
ATCATGTATGGTATTCCACGCTGTGTTATCGGTGAGAACGTTAATTTC
AAAAGTAAGGGCGAGAAATATTTACAAACTAGAGGTCACGAGGTTGTT
GTTGTTGACGATGAGAGGTGTAAAAAGCTCATGAAACAATTTATCGAT
GAAAGACCTCAGGATTGGTTTGAAGATATTGGTGAGTAG
```

In other certain embodiments of the invention, the molecular switch comprises a polypeptide comprising the amino acid sequence of SEQ ID NO: 2. IN SEQ ID NO: 2, shown below, the segment origination from CH1 is shown in bold and underlined. The corresponding nucleic acid sequence is shown as SEQ ID NO: 4.

```
                                                    SEQ ID NO: 2
MVTGGMAS DPEKRKLIQQQLVLLLHAHKCQRREQANGEVRQCNLPHCR
TMKNVLNHMTHCQSGKSCQVAHCASSRQIISHWKNCTRHDCPVCLPLK
NAGG WDQKGMDIAYEEALLGYKEGGVPIGGCLINNKDGSVLGRGHNMR
FQKGSATLHGEISTLENCGRLEGKVYKDTTLYTTLSPCDMCTGAIIMY
GIPRCVIGENVNFKSKGEKYLQTRGHEVVVVDDERCKKLMKQFIDERP
QDWFEDIGE
```

```
                                                    SEQ ID NO: 4
ATGGTGACAGGGGGAATGGCAAGCGATCCGGAAAAACGTAAACTGATC
CAGCAGCAGCTGGTGCTGCTGCTGCATGCTCACAAATGTCAGCGTCGT
GAACAGGCAAACGGCGAAGTACGTCAGTGCAACCTGCCGCACTGCCGT
ACAATGAAAAATGTACTGAACCACATGACCCACTGCCAGAGCGGTAAA
AGCTGCCAGGTAGCTCACTGCGCATCTTCTCGCCAGATTATCTCTCAC
TGGAAAAACTGCACCCGTCACGATTGCCCGGTTTGCTTGCCGCTCAAG
AACGCTGGTGGCTGGGATCAGAAGGGTATGGACATTGCCTATGAGGAG
GCGCTCTTAGGTTACAAAGAGGGTGGTGTTCCTATTGGCGGATGTCTT
ATCAATAACAAAGACGGAAGTGTTCTCGGTCGTGGTCACAACATGAGA
TTTCAAAAGGGATCCGCCACACTACATGGTGAGATCTCCACTTTGGAA
AACTGTGGGAGATTAGAGGGCAAAGTGTACAAAGATACCACTTTGTAT
ACGACGCTGTCTCCATGCGACATGTGTACAGGTGCCATCATCATGTAT
GGTATTCCACGCTGTGTTATCGGTGAGAACGTTAATTTCAAAAGTAAG
GGCGAGAAATATTTACAAACTAGAGGTCACGAGGTTGTTGTTGTTGAC
GATGAGAGGTGTAAAAAGCTCATGAAACAATTTATCGATGAAAGACCT
CAGGATTGGTTTGAAGATATTGGTGAGTAG
```

Fusion molecules can further comprise domain sequences, as described above, in addition to insertion and acceptor sequences. Such domains can comprise states which may or may not be coupled with the states of the other portions of the fusion molecule.

In certain examples, additional sequences also can be included as part of the fusion molecule which do not alter substantially the states of the insertion sequence or acceptor sequence portion of the fusion molecule. For example, affinity tag sequences can be provided to facilitate the purification or isolation of the fusion molecule. Thus, His6 tags can be employed (for use with nickel-based affinity columns), as well as epitope tags (e.g., for detection, immunoprecipitation, or FACS analysis), such as myc, BSP biotinylation target sequences of the bacterial enzyme BirA, flu tags, lacZ, GST, and Strep tags I and II. Nucleic acids encoding such tag molecules are commercially available.

Stability sequences can be added to the fusion molecule to protect the molecule from degradation (e.g., by a protease).

Suitable stability sequences include, but are not limited to, glycine molecules incorporated after the initiation methionine (e.g., MG or MGG) to protect the fusion molecule from ubiquitination; two prolines incorporated at the C-terminus (conferring protection against carboxypeptidase action), and the like.

For example, the fusion molecule can include a linking or tethering sequence between insertion and acceptor sequences or between insertion or acceptor sequences and other domain sequences. For example, useful linkers include glycine polymers, glycine-serine polymers, glycine-alanine polymers, alanine-serine polymers, alanine polymers, and other flexible linkers as are known in the art (see, e.g., Huston, et al., 1988, Proc. Natl. Acad. Sci. USA 85: 4879; U.S. Pat. No. 5,091,513, incorporated by reference in its entirety herein).

These additional sequences can be included to optimize the properties of the fusion molecules described herein Fusion molecules according to the invention can be expressed in a variety of host cells, including, but not limited to: prokaryotic cells (e.g., *E. coli, Staphylococcus* sp., *Bacillus* sp.); yeast cells (e.g., *Saccharomyces* sp.); insect cells; nematode cells; plant cells; amphibian cells (e.g., *Xenopus*); fish cells (e.g., zebrafish cells); avian cells; and mammalian cells (e.g., human cells, mouse cells, mammalian cell lines, primary cultured mammalian cells, such as from dissected tissues).

The molecules can be expressed in host cells isolated from an organism, host cells which are part of an organism, or host cells which are introduced into an organism. In one aspect, fusion molecules are expressed in host cells in vitro, e.g., in culture. In another aspect, fusion molecules are expressed in a transgenic organism (e.g., a transgenic mouse, rat, rabbit, pig, primate, etc.) that comprises somatic and/or germline cells comprising nucleic acids encoding the fusion molecules.

Fusion molecule also can be introduced into cells in vitro, and the cells (e.g., such as stem cells, hematopoietic cells, lymphocytes, and the like) can be introduced into the host organism. The cells may be heterologous or autologous with respect to the host organism. For example, cells can be obtained from the host organism, fusion molecules introduced into the cells in vitro, and then reintroduced into the host organism.

The invention features vectors that comprise the polynucleotides as described herein, and cells that are transformed with said vectors. The cells can be, for example *E. coli* cells or mammalian cells.

Methods of Using Molecular Switches

In one aspect, the invention provides a method for using a molecular switch to modulate a cellular activity. The cellular activity can include an enzyme activity, the activity of one or more cellular pathway molecules, the transduction of a signal, and the like. Modulation may direct, e.g., the switch itself may alter the activity, or indirect, e.g., the switch may function by delivering a bio-effective molecule to the cell which itself modulates the activity. Modulation can occur in vitro (e.g., in cell culture or in a cell extract) or in vivo (e.g., such as in a transgenic organism). Molecular switches comprising fusion polypeptides also can be administered to a cell by delivering such molecules systemically (e.g., through intravenous, intramuscular, or intraperitoneal injections, or through oral administration of either the polypeptides themselves or nucleic acids encoding the polypeptides) or locally (e.g., via injection into a tumor or into an open surgical field, or through a catheter or other medical access device, or via topical administration). The method of administration is not limiting in the present invention, and can be by any method envisioned by the skilled practitioner.

In one aspect, molecular switches are used to conditionally modulate an enzymatic activity in a cell. For example, a switch molecule can be introduced into a cell that comprises an insertion sequence or acceptor sequence which provides the enzymatic activity. Catalysis by the insertion or acceptor sequence is coupled to the response of the respective other portion of the fusion molecule to a signal, such as binding of the other portion to a molecule (e.g., such as an agent administered to the cell or a naturally occurring small molecule), exposure of the cell to particular chemical conditions (e.g., such as pH), electrical conditions (e.g., potential differences), optical conditions (e.g., exposure of the cell to light of specific wavelengths), magnetic conditions and the like.

In a particular aspect, the present invention provides a method to convert a prodrug into a toxin in a cell that expresses a cancer specific marker comprising expressing a polypeptide comprising a prodrug activating enzyme and a protein that binds a cancer specific marker in a cell; and treating the cells with a prodrug, wherein the protein that binds the cancer specific marker binds the marker in a cell that expresses the marker and activates the prodrug activating enzyme, thereby converting the prodrug into a toxin.

The present invention described a novel approach to GDEPT using switches that uses gene delivery to deliver the therapeutic switch gene that can activate the prodrug. The present approach is novel as it utilizes a targeting strategy distinct from transductional and transcription targeting. The present approach does not necessarily require specific delivery to target cells or activation of the gene in target cells because the catalytic activity that activates the prodrug is preferably regulated at the enzyme level and is preferably activated only in the target cells. Accordingly, the present invention allows methods to efficiently deliver genes to the target cells to be used (methods that may lack cell-specificity), since expression of the therapeutic protein in non-target cells will not result in prodrug activation since the cells lack the signal to activate the enzyme.

In certain embodiments, the prodrug is selected from the group consisting of fluorocytosine (5-FC), ganciclovir, 5-(Aziridin-1-yl)-2,4-dinitrobenzamide (CB 1954), methotrexate-alanine, ifosfamide, anygdalin, cephalosporin-derivatized prodrugs.

In particular examples, the prodrug is 5-FC.

In particular, the invention provides a method to convert 5-FC into 5-fluorouracil (5-FU) in a cell that expresses a cancer specific marker, wherein the marker is HIF-1a, comprising expressing a polypeptide comprising a cytosine deaminase (CD) and a CH1 domain in a cell; and treating the cells with a prodrug, wherein the CH1 domain activates cytosine deaminase in cells that express HIF-1a, thereby converting 5-FC into 5-FU.

Fluorouracil is a pyrimidine analog and belongs to a group of drugs known as antimetabolites. It is typically used to treat colon cancer, rectal cancer, breast cancer, stomach cancer and pancreatic cancer, although it is also used to treat ovarian cancer, cervical cancer, and bladder cancer. As a pyrimidine analogue, 5-FU is transformed inside the cell into different cytotoxic metabolites which are then incorporated into DNA and RNA, finally inducing cell cycle arrest and apoptosis by inhibiting the cell's ability to synthesize DNA. It is an S-phase specific drug and only active during certain cell cycles. In addition to being incorporated in DNA and RNA, the drug has been shown to inhibit the activity of the exosome complex, an exoribonuclease complex of which the activity is essential for cell survival. 5-FC is a prodrug that is converted into 5-FU in the tissues.

Accordingly, after the prodrug 5-FC is administered, the major metabolite of 5-FU, having anticancer activity in its own right, appears in the subject. In certain preferred embodiments then 5-FC and 5-FU are thus each, and together, responsible for the therapeutic benefit of the method of the invention. Accordingly, a therapeutically effective amount of a dose can be an amount that, after one or more cycles of administration results in a therapeutic benefit. The therapeutic benefit from the treatment method of the present invention can be observed in responding subjects as soon as a few days, or 1, 2, 3, 4, 8, 12, 16, 20, or 24 weeks from the start of treatment (e.g. the first administration of the pharmaceutical formulation).

The present invention can be used to treat patients with cancer who have failed one or more prior anti-cancer therapy regimens. These prior anti-cancer regimens include, but are not limited to, monotherapy, combination therapy, surgery, and radiation therapy.

In certain embodiments, the states of the fusion molecules are coupled to a signal, such as the presence of an exogenous or endogenous binding molecules to which either the insertion sequence or acceptor sequence binds. The ability of the fusion molecule to control a pathway can be monitored by examining the expression and/or activity of pathway molecules which act downstream of a pathway molecule whose expression and/or activity is being modulated/controlled by the fusion molecule. Preferably, control of the pathway is coupled to the presence of the signal, e.g., binding of the fusion molecule to the exogenous or endogenous binding molecule, the presence of particular electrical or chemical properties of a cell, the presence or absence of particular wavelength(s) of light, and the like.

Preferred fusion molecules of the present invention are provided that deliver a bio-effective molecule, e.g. a molecule comprising a prodrug activating enzyme and a protein that binds a specific marker in a cell, for example a cancer specific marker. For example, the fusion molecule comprises an insertion or acceptor sequence which binds to the bio-effective molecule, while the respective other portion of the fusion binds to a cellular marker that is a signature of a pathology, e.g., a small molecule, polypeptide, nucleic acid, metabolite, whose expression (presence or level) is associated with the pathology. Preferably, the fusion molecule releases the bio-effective molecule only in the presence of the marker of the pathology.

In a preferred aspect, the invention provides a method of treating cancer in a subject comprising contacting one or more cells in a subject with a polypeptide comprising a prodrug activating enzyme and a protein that binds a cancer specific marker, and treating the subject with a prodrug, wherein the protein that binds the cancer specific marker binds the marker in a cell that expresses the marker and activates the prodrug activating enzyme, thereby converting the prodrug into a toxin, thereby treating cancer in a subject.

The method can be used to treat new and existing tumors, growths and polyps. Benign tumors, growths and polyps include squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocytic nevus, fibroma, myxoma, lipoma, leiomyoma, rhabdomyoma, benign teratoma, meangioma, osteoma, chondroma and meningioma. Cancerous tumors, growth and polyps include squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, osteosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The invention includes benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells.

Preferably, the invention encompasses treating or preventing the following cancers: lung, breast, prostate and colon cancer.

In a further aspect, a fusion molecule is provided for regulating an activity of a nucleic acid regulatory sequence in vitro or in vivo. Activities which can be regulated include transcription, translation, replication, recombination, supercoiling, and the like. Preferably, fusion molecules are selected in which binding of the insertion sequence or acceptor sequence of the fusion molecule to the nucleic acid regulatory sequence is coupled to the response of the respective other sequence of the fusion molecule to a signal.

Preferably, the signal is in a cell that expresses a cancer marker.

Such fusion molecules can be used to create cells with conditional knockouts or knock-ins of a gene product whose expression is mediated by the activity of the nucleic acid regulatory sequence to which the fusion molecule binds, e.g., by providing or withdrawing the signal as appropriate. In one aspect, the signal is a drug or therapeutic agent. In another aspect, the signal is a change in pH, a change in cellular potential, or a change in exposure of a cell (and/or organism) to light. For example, a probe for delivering particular wavelengths of light can be used to provide a highly localized signal to a cell expressing a fusion molecule in vivo.

The fusion polypeptides may be used to modulate a cellular response by conditionally providing a pair of fusion polypeptides to a cell to mediate the response. For example, the pair of fusion polypeptides can comprise a binding activity, an enzymatic activity, a signaling activity, a metabolic activity, and the like. In one aspect, the pair of fusion polypeptides modulate transcription, translation, or replication of the cell and/or alters a cellular phenotype in response to a signal Insertion Libraries In one aspect, the invention includes a method for assembling a fusion molecule comprising randomly circularly permuting an insertion sequence and inserting the insertion sequence into an acceptor sequence. Exemplary insertion and acceptor sequences are described herein, and generally include any two sequences desired to be functionally combined in a fusion molecule to form a molecular switch.

By using a combinatorial approach, a plurality of potential switches is created from which to select switches with optimized characteristics. This method is advantageous over existing domain insertion methods in that vastly increased numbers of geometric configurations between the acceptor sequence and the insertion sequence can be generated and made available for testing. As discussed, the switching behavior achieved to date by existing methods is generally modest (i.e., less than about 2-fold effect). See, for example, PCT Publication WO 03/078575, herein incorporated by reference, and Guntas and Ostermeier (2004).

Accordingly, in one aspect, the invention provides a method of making a molecular switch comprising providing a DNA library comprising one or more nucleotide sequences coding for the CH1 domain and one or more nucleotide sequences coding for the CD domain, performing circular permutation of the CH1 domain, and randomly inserting the CH1 domain into the CD domain, thereby making a molecular switch.

Circular permutation of at least one of the genes (in this case the insert gene) is central to the method. Although circular permutation of the insert gene is shown, circular permutation of the acceptor sequence, or both sequences, is within the invention.

As is known in the art, a circularly permuted protein has its original N- and C-termini fused and new N- and C-termini created by a break elsewhere in the sequence. The insert gene is circularly permutated using any suitable technique. Exemplary techniques for circular permutation by chemical or genetic methods include but are not limited to those described for example by Goldenberg and Creighton (1983), and Heinemann and Hahn (1995). A particularly preferred genetic method for random circular permutation is that of Graf and Schachmann (1996). See also Ostermeier and Benkovic (2001).

A number of different strategies can be used to create the fusion molecules of the instant invention, as described herein. The strategies are generally applicable to creating any desired molecular switches, and are illustrated several Examples herein, using exemplary fusions that combine sequences from two non-homologous proteins, for example the beta.-lactamase (BLA)-maltose binding protein (MBP) fusion proteins that responds to a signal (i.e., maltose). As described, the BLA-MBP fusion proteins can act as molecular switches, for example by functioning as BLA enzymes only in the presence of maltose.

A preferred method of randomly circularly permuting a sequence can generally include the following steps:
(i) isolating a linear fragment of double-stranded DNA of the gene to be randomly circularly permuted with a linker sequence and flanking compatible ends;
(ii) cyclizing the DNA fragment by ligation under dilute conditions;
(iii) randomly linearizing the cyclized gene, for example using digestion by a nuclease such as DNaseI under conditions in which the enzyme, on average, makes one double-strand break;
(iv) repairing nicks and gaps, for example using enzymes such as DNA polymerase and DNA ligase, respectively; and
(v) ligating the fragment into a desired vector comprising the acceptor sequence by blunt end ligation, to create a library of randomly circularly permuted sequences.

Preferred methods for preparing cyclized genes include a step of adding DNA that codes for a "linker" to link the original N- and C-termini. Any suitable linker sequences can be used for this purpose. Preferred methods of cyclizing a gene utilize linkers such a "DKS linker" (Osuna et al., 2002) or a flexible pentapeptide linker such as a "GSGGG linker" having the amino acid sequence GSGGG.

Generally, the gene fragment of interest is amplified by a suitable technique such as polymerase chain reaction (PCR) under conditions resulting in flanking of the selected sequence by restriction enzyme site sequences coding for the linkers, and is then cloned into a suitable vector such as pGem T-vector (Promega).

In certain preferred embodiments, the CH1 domain comprises a linker. In certain preferred embodiments, the linker may be selected from the group consisting of GSGGG, (GSGGG)2 and (GSGGG)3.

The fragments to be cyclized are then released from the cloning vector by digestion with a suitable restriction enzyme and purified, for example by agarose gel electrophoresis. Cyclizing is achieved, for example, by treating with a ligase such as T4 DNA ligase. The cyclized (circular) fragments are subsequently purified and subjected to circular permutation (step iii above). The circularized genes are randomly linearized, by subjecting them to cleavage with a digestion enzyme that makes on average one double-strand break in the circularized DNA. A preferred enzyme for use in this step is a nuclease. A particularly preferred enzyme is DNaseI. The conditions for nuclease digestion can be determined experimentally by varying the amount of enzyme added and analyzing the digested products by agarose gel electrophoresis. Generally, approximately 1 milliunit of DNaseI per microgram of DNA (at a concentration of 10 micrograms per ml) for an 8-minute digestion at 22° C. is suitable, but will vary somewhat for each library. See also Example 1 for further details of suitable conditions for the digestion step. In addition to digestion by nucleases (e.g., DNAse, S1, exonucleases, restriction endonucleases and the like), other methods for introducing breaks in sequences can be used. For example, mechanical shearing, chemical treatment, and/or radiation can be used. Generally, the method for introducing breaks is not intended to be limiting.

In one aspect, libraries comprising a plurality of library members are provided by the invention. Each library member comprises a first nucleic acid sequence encoding a first polypeptide having a first state, the first nucleic acid sequence having been randomly circularly permuted and inserted into a second nucleic acid encoding a second polypeptide having a second state. The libraries can be constructed in any suitable manner known in the art of molecular biology.

In one preferred type of library, the randomly circularly permuted sequences are randomly inserted into acceptor sequences, a strategy which maximizes the number of possible combinations of insertion and acceptor sequences. Several different strategies can be used to make such random insertion libraries.

In one aspect, libraries are constructed in which an insertion sequence has been randomly inserted into an acceptor sequence. Preferably, such libraries are generated by randomly inserting a nucleic acid fragment encoding an insertion sequence into a nucleic acid fragment encoding an acceptor sequence.

Accordingly, the invention provides a method of making a molecular switch comprising providing a DNA library comprising one or more nucleotide sequences coding for the CH1 domain and one or more nucleotide sequences coding for the CD domain, and randomly inserting the CH1 domain into the CD domain, and thereby making a molecular switch.

Preferably, the inserting is at an insertion site. The linker may be, for example, selected from the group consisting of: GGS, GGGGS.

Random insertion can be carried out by, for example, insertion via transposons and insertion after a random double stranded break in DNA using one or a combination of nucleases. A variety of transposons have been used to deliver short, in-frame insertions of 4-93 amino acids (e.g., Hayes and Hallet, 2000, Trends Microbiol. 8: 571-7; and Manoil and Traxler, 2000, Methods 20: 55-61). However, although transposons are an efficient method for delivering an insertion, insertion methods are preferred which create libraries with direct insertions, deletions at the insertion site, or variability in the amount of deletions or tandem duplication or variability in the distribution of direct insertions, deletions and tandem duplications.

Random insertion using nuclease treatment, on the other hand, can create such libraries. These methods typically are used for the insertion of short sequences into a target gene for example during linker scanning mutagenesis. These methods generally differ in the strategy used to produce a random, double-strand break in supercoiled plasmid DNA containing the gene to be inserted.

Any suitable procedure for randomly inserting a first sequence into second sequence can be used. Exemplary methods are described, for example, in PCT Publication WO 03/078575, herein incorporated by reference. As discussed, the use of BLA and MBP as respective insertion and acceptor sequences, and the use of particular vectors are merely exemplary; potentially any two proteins can be functionally coupled in this manner following random circular permutation of one or both sequences.

To prepare a random insertion library, a target vector comprising the nucleic acid encoding the acceptor polypeptide is preferably randomly linearized. For linearization, a variety of different nucleases and digestion schemes can be used. For example, the vector may be exposed to DNase/Mn2+ digestion followed by polymerase/ligase repair; S1 nuclease digestion followed by polymerase/ligase repair; or S1 nuclease digestion which is not repaired. The three schemes differ in (a) the methods used to create the random double-stranded break in the target plasmid and (b) whether or not the nucleic acid (e.g., DNA) is repaired by polymerase/ligase treatment, or other methods. However, it should be apparent to those of skill in the art that any method of introducing breaks into a DNA molecule can be used (e.g., such as digestion by mung bean nucleases, endonucleases, restriction enzymes, exposure to chemical agents, irradiation, and/or mechanical shearing) and that the methods of introducing breaks described above are not intended to be limiting.

Preferably, digestion is controlled such that a significant fraction of DNA is undigested in order maximize the amount of linear DNA that has only one double strand break. Key features for optimizing DNase I digestion include the use of Mg2+ free DNaseI (Roche Molecular Biochemicals), a digestion temperature of 22C and 1 mM $Mn^{2+}$ instead of Mg2+ to increase the ratio of double strand breaks to nicks (see, e.g., as described in Campbell and Jackson, 1980, J. Biol. Chem. 255: 3726-35).

The DNA can be repaired using methods known in the art, for example, using T4 DNA ligase and T4 DNA polymerase (see, e.g., Graf and Schachman, 1996, Proc. Natl. Acad. Sci. USA 93: 11591-11596), and dephosphorylated. Ligation with nucleic acids encoding the insert is performed and nucleic acids (e.g., library members) are collected.

In one aspect, transformants are selected which express a reporter gene included in the target vector, such as a drug resistance gene to initially screen for fusion molecules. Alternatively, or additionally, transformants can be selected in which the state of the insertion sequence is coupled to the state of the acceptor sequence. Thus, in one aspect, the existence of each state is assayed for, as is the dependence of each state on the existence of one or more other states. States may be assayed for simultaneously, or sequentially, in the same host cell or in clones of host cells. Fusion molecules also can be isolated from host cells (or clones thereof) and their states can be assayed for in vitro.

For example, in one aspect, the enzymatic activity of an insertion sequence or acceptor sequence is assayed for at the same time that the binding activity of the respective other portion of the fusion is evaluated to identify fusion molecules in which enzymatic activity is dependent on binding activity.

In the present invention, the fusion molecules comprise a prodrug activating enzyme and a protein that binds a cancer specific marker.

Accordingly, in certain preferred embodiments, libraries are screened for fusion molecules which bind to a molecule, such as a bio-effective molecule (e.g., a drug, therapeutic agent, toxic agent, or agent for affecting cellular physiology). The bound fusion molecule is exposed to a cell, and the ability of the fusion molecule to be localized intracellularly is determined. In other further embodiments, release of the bio-effective molecule in response to intracellular localization also is determined.

For example, a cell can be transiently permeabilized (e.g., by exposure to a chemical agent such as Ca2+ or by electroporation) and exposed to a fusion molecule associated with the bio-effective molecule (e.g., bound to the bio-effective molecule), allowing the fusion molecule and bound molecule to gain entry into the cell. The ability of the fusion molecule to localize to an intracellular compartment (e.g., to the endoplasmic reticulum, to a lysosomal compartment, nucleus, etc.) along with the bio-effective molecule can be monitored through the presence of a label (e.g., such as a fluorescent label or radioactive label) on the fusion molecule, bio-effective molecule, or both. The label can be conjugated to the fusion molecule and/or the bio-effective molecule using routine chemical methods known in the art. A label also may be provided as part of an additional domain of the fusion molecule. For example, the fusion molecule can comprise a GFP polypeptide or modified form thereof. The localization of the label (and hence the fusion molecule and/or bio-effective molecule) can be determined for example using light microscopy. Release of the bio-effective molecule can be monitored by lysing the cell, immunoprecipitating the fusion molecule, and detecting the amount of labeled bio-effective molecule in the precipitated fraction.

In one aspect, the cell need not be permeabilized to allow entry of the fusion molecule because the fusion molecule comprises a signal sequence that enables the fusion molecule to traverse the cell membrane. Intracellular transport of the bio-effective molecule can be monitored by labeling the bio-effective molecule and examining its localization using light microscopy, FACs analysis, or other methods routine in the art.

In another aspect, insertion libraries are screened for fusion molecules which comprise a prodrug activating enzyme and a protein that binds a cancer specific marker, and when the fusion molecule binds to a cellular marker of a pathological condition. Thus, in one aspect, fusion molecules associated with a bio-effective molecule are contacted with cells expressing such a marker and the ability of the fusion molecules to specifically bind to the cell is assayed for, as well as the ability of the fusion molecule to release the bio-effective molecule in response to such binding. For example, as above, either, or both, the fusion molecule and the bio-effective molecule can be labeled and the localization of the molecules determined. The action of the bio-effective molecule also can be monitored (e.g., the effect of the bio-effective molecule on the cell can be monitored).

Insertion libraries can be screened for polypeptides comprising a prodrug activating enzyme and a protein that binds a cancer specific marker which can switch from a non-toxic state to a toxic state upon binding to a cellular marker of a pathology. Fusion molecules can be selected which specifically bind to cells expressing the marker, and the effect of the fusion molecules on cell death can be assessed. Cell death can be monitored using methods routine in the art, including, but not limited to: staining cells with vital dyes, detecting spectral properties characteristic of dead or dying cells, evaluating the morphology of the cells, examining DNA fragmentation, detecting the presence of proteins associated with cell death, and the like. Cell death also can be evaluated by determining the $LD_{50}$ or $LC_{50}$ of the fusion molecule.

In other exemplary embodiments, the insertion library is screened for fusion molecules which comprise a molecular switch for controlling a cellular pathway. Preferably, the states of the insertion sequence and acceptor sequence in the fusion molecules are coupled and responsive to a signal such that in the presence of the signal, the state of either the insertion sequence or the acceptor sequence modulates the activity or expression of a molecular pathway molecule in a cell. A signal can be the presence, absence, or level, of an exogenous or endogenous binding molecule to which either the insertion sequence or acceptor sequence binds, or it can be a condition (e.g., chemical, optical, electrical, etc.) in an environment to which the fusion molecule is exposed. The ability of the fusion molecule to control a pathway can be monitored by examining the expression and/or activity of pathway molecules which act downstream of a pathway molecule whose expression and/or activity is being modulated.

In another aspect, fusion molecules are selected in which either the prodrug activating enzyme or the protein that binds a cancer specific marker (e.g. the insertion or the acceptor sequence) binds to a nucleic acid molecule. For example, the ability of the fusion molecules to bind to a nucleic acid immobilized on a solid phase can be monitored (e.g., membrane, chip, wafer, particle, slide, column, microbead, microsphere, capillary, and the like). Preferably, fusion molecules are selected in which nucleic acid binding activity is coupled to a change in state of the respective other sequence of the fusion molecule. For example, nucleic acid binding activity can be coupled to the binding activity of another portion of the fusion molecule, catalysis by the other portion, the light emitting function of the other portion, electron transferring ability of the other portion, ability of the other portion to change conformation, and the like. Preferably, nucleic acid binding activity is coupled to the response of the fusion molecule to a signal.

Nucleic acid binding activity also can be monitored by evaluating the activity of a target nucleic acid sequence to which the fusion molecule binds. For example, in one aspect, the fusion molecule binds to a nucleic acid regulatory sequence which modulates the activity (e.g., transcription, translation, replication, recombination, supercoiling) of another nucleic acid molecule to which the regulatory sequence is operably linked. The nucleic acid regulatory molecule and its regulated sequence can be provided as part of a nucleic acid molecule encoding the fusion molecule or can be provided as part of a separate molecule(s). The nucleic acid binding activity can be monitored in vitro or in vivo. The ability of fusion molecules to bind to a nucleic acid can also be determined in vivo using one-hybrid or two-hybrid systems (for example, see, Hu, et al., 2000, Methods 20: 80-94).

In certain aspects, fusion molecules are selected which bind to a known regulatory sequence or a sequence naturally found in a cell. In other aspects, a sequence which is not known to be a regulatory sequence in a cell is selected for. Preferably, such a sequence binds to the fusion molecule and modulates the activity of another nucleic acid (in cis or in trans), Thus, the fusion molecule can be used to select for novel nucleic acid regulatory sequences. Preferably, the fusion molecule modulates the regulatory activity of the nucleic acid molecule in response to a signal, as described above.

In still a further aspect, the insertion library is screened for fusion molecules which are sensor molecules. Preferably, fusion molecules are screened for in which either the insertion sequence or acceptor sequence binds to a target molecule and wherein the respective other portion of the fusion molecule generates a signal in response to binding. Signals can include: emission of light, transfer of electrons, catalysis of a substrate, binding to a detectable molecule, and the like. To assay for such fusions, members of the library can be screened in the presence of the target molecule (e.g., in solution, or immobilized on a solid support) for the production of the signal.

In certain preferred embodiments, the fusions in which cellular enzyme activity is modulated by the ligand of the sensing domain are identified through genetic selections. In further related embodiments, the genetic selection is a selection for HIF-1a activation of deaminase activity.

The following examples are offered by way of illustration and not by way of limiting the remaining disclosure.

EXAMPLES

The present invention describes a novel protein engineering strategy by combining the domains of two independent proteins into a single hybrid protein. As a proof of principle, the present inventors have created maltose-activated beta-lactamases by combining maltose binding protein with TEM1 beta-lactamase. In these switch proteins, beta-lactamase enzyme activity is increased 500-fold in the presence of maltose, but they are inactive in the absence of maltose.

Accordingly, a therapeutic protein switch is created in the same fashion as the maltose-activated proteins, by combining a prodrug activating enzyme and a protein that binds a cancer-specific marker. The examples describe hypoxia inducible factor-1 alpha (HIF-1a) as the cancer-specific marker. HIF-1a is absent in normal tissue due to rapid degradation, but is overexpressed within many types of cancer. Accordingly, the therapeutic protein will be inactive in normal tissue and will be activated by HIF-1a to convert the prodrug into a toxin in cancer cells. The present examples describe the use of the HIF-1a binding domain from the p300 protein and a cytosine deaminase to make our therapeutic switch.

Cytosine deaminase (CD) is an enzyme that is able to convert the relatively harmless 5-fluorocytosine (5-FC) prodrug into the toxic 5-fluorouracil (5-FU). Accordingly, cancer cells that overexpress HIF-1a will activate the protein switch to convert 5-FC into 5-FU, thereby killing the cancer cells. This therapeutic protein could have the potential to be used in a treatment method that is analogous to GDEPT, but will have superior "killing" efficiency with reduced side-effects because the selectivity of our method arises at the molecular level.

The approach to GDEPT described herein using switches makes use of gene delivery to deliver the therapeutic switch gene that can activate the prodrug and thus shares all of the advantages inherent in GDEPT. This approach is novel since it utilizes a targeting strategy distinct from transductional and transcription targeting. The approach described herein does not necessarily require specific delivery to target cells or activation of the gene in target cells because the catalytic activity that activates the prodrug will be regulated at the enzyme level and will be activated only in the target cells. This allows superior methods that efficiently deliver genes to the target cells to be used (methods that may lack cell-specificity), since expression of the therapeutic protein in non-target cells will not result in prodrug activation since the cells lack the signal to activate the enzyme.

Although the described targeting approach is distinct from transductional and transcriptional targeting, it is complementary to these targeting approaches. Accordingly, in certain preferred embodiments, it may be possible to combine these approaches to get a double or triple layer of specificity: at the gene delivery, at the gene transcription and at the enzyme levels.

Example 1

Creation of Protein Switches by In Vitro Recombination of Non-Homologous Genes

A general strategy was developed that is theoretically amenable to a wide variety of input and output functions that can create switches with large changes in output both in vitro and in vivo. In this approach, natural or engineered proteins with the desired input and output functions are combined in a systematic fashion to create libraries of recombined proteins. From these libraries, switches with coupled functions are suitably identified using genetic selection and screening. Such an approach is inspired by the evolutionary mechanism of domain recombination (68), a major facilitator in the natural evolution of protein function (69). Domain recombination strategies have been applied to the construction of switches (22-30), but the very limited manner in which the domains were recombined has restricted the success of this approach. A diverse exploration of fusion geometries between two proteins would enable the creation of switches with superior properties. An approach was taken that can be conceptualized, for example, as "rolling" the two proteins across each others surface and fusing them through peptide bonds at the points where their surfaces meet. A novel, homology-independent, combinatorial method for recombining genes that samples such a structural space was developed. This method involves two types of recombination (1) the random insertion of one gene into another (i.e. random domain insertion) and (2) random circular permutation of one of the genes (see FIG. 3). For a gene that has been circular permutated, the corresponding protein has a linker peptide joining the original N- and C-terminus of the protein and has a new N- and C-termini elsewhere in the structure. This strategy was utilized to combine the enzyme TEM-1 13-lactamase (BLA) and the ligand-binding protein maltose binding protein (MBP) and create a family of allosteric beta-lactamases that are modulated by maltose (6-8).

It was first demonstrated by the present inventors that one could randomly insert the BLA gene into the MBP gene and, through selection/screening strategies, create switches (8). This was the first demonstration of the creation of an allosteric enzyme by the covalent linkage of non-interacting proteins with the prerequisite effector-binding and catalytic functionalities, respectively.

Figure 3:
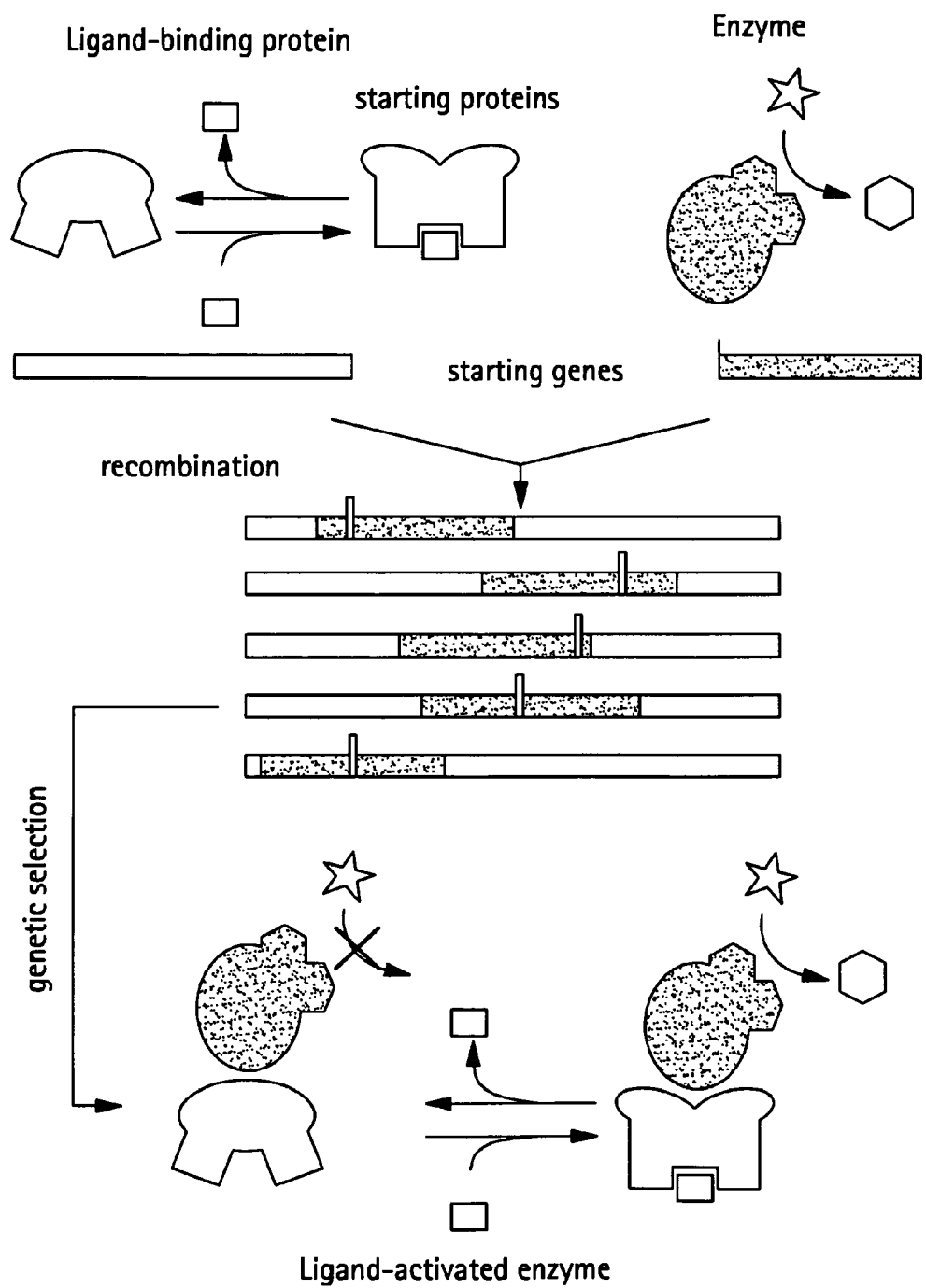
FIG. 3 is a schematic showing the creation of ligand-activated enzymes (switches) by in vitro recombination. The genes encoding a ligand-binding domain and an enzyme are subjected to a recombination process that involves random circular permutation of the enzyme gene and random insertion of the enzyme gene into the ligand-binding domain gene. This library is then subject to genetic selection and/or screening to identify those library that are switches in which their enzyme activity depends on the presence of bound-ligand. Such switches are ligand-activated enzymes.

The present inventors have described simultaneous random circular permutation of the BLA gene followed by random insertion of the circularly permuted library into the MBP gene, as shown in FIG. 3. This approach was very successful (for switch RG13, maltose-binding increased BLA catalytic efficiency 25-fold). The importance of this result stems not only from the high level of switching, but also from the other exemplary properties the switch possessed. Specifically, the switch only responded to known ligands of MBP, it was instantaneously reversible (upon removal of maltose, the BLA rate decreased back to the low level), it was modular (mutations known to increase the affinity of MBP for maltose created more sensitive switches) and it conferred to E. coli a novel phenotype: maltose-dependent resistance to beta-lactam antibiotics. The latter experiment illustrates two key applications of these switches: (1) their ability to "rewire" the cell (antibiotic resistance is coupled to maltose concentration) and (2) their potential for sensing applications (our E. coli cells are engineered "biosensors" for maltose).

Figure 4:
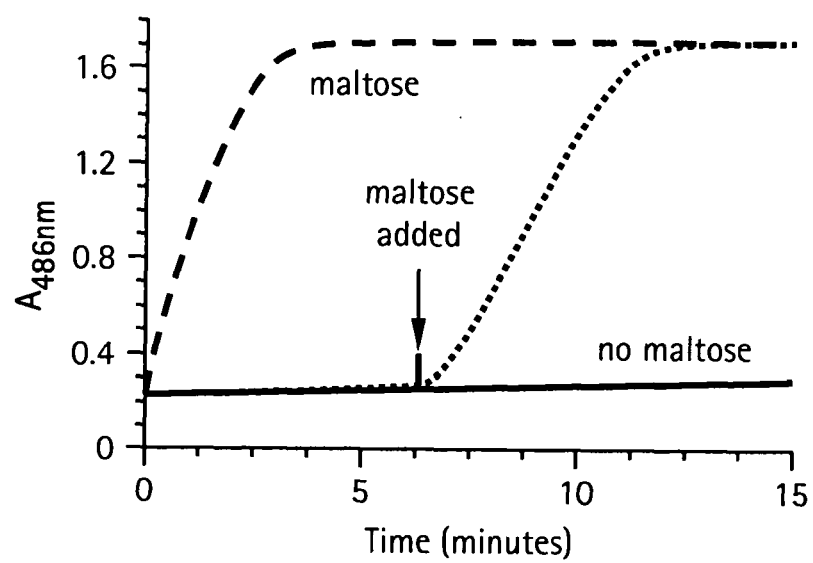
FIG. 4 is a graph showing beta-lactam hydrolysis catalyzed by switch MBP317-347 in the presence and absence of maltose. During the enzymatic hydrolysis of the BLA substrate nitrocefin, formation of product is monitored by absorbance at 486 nm. The reaction was started by the addition of nitrocefin at time zero to samples lacking or containing 5 mM maltose. 5 mM maltose was added to the reaction at about 6 minutes. At an absorbance of about 1.7, all of the nitrocefin has been converted to product.

Natural allosteric proteins often have modest (<10-fold) differences in function between the effector-bound and effector-unbound states. However very large differences in activity between the two states would be advantageous for many applications of protein switches. In addition, it would be beneficial for the switches to exhibit complex behavior in their interaction with ligands (e.g. exhibit both agonistic and antagonistic effects). Using an iterative strategy involving random circular permutation and random insertion several switches were created that approach being on/off in nature (6). For one switch (MBP317-347) maltose acted as an agonist, increasing beta-lactamase activity up to 600-fold (see FIG. 4). beta-cylcodextrin acted as antagonist preventing maltose-activation. The creation of these switches was facilitated by a new directed evolution algorithm for non-homologous recombination that was developed for efficiently exploring the sequence space comprised of the possible fusions of the two proteins. In addition, the modular nature of these switches as demonstrated by redesigning one switch to have a new effector: sucrose (6). The binding pocket of the maltose binding protein (MBP) domain was randomized and sucrose-activated switches were identified using a genetic selection uniquely made possible by the properties of the switch itself. Cells bearing these mutated switches were plated in the presence of sucrose at concentrations of beta-lactam antibiotic that normally only allow growth if maltose is present. A switch variant that is able to bind sucrose will adopt its more active conformation and allow the cell form a colony. Using this strategy, the present inventors created a sucrose-activated switch with affinities for sucrose equivalent to that of MBP for maltose. The transplantation of these mutations into wild-type MBP converted MBP into a 'sucrose-binding protein. Thus, the switches can also be used a selection system for new ligand-binding functionalities.

Figure 5A:
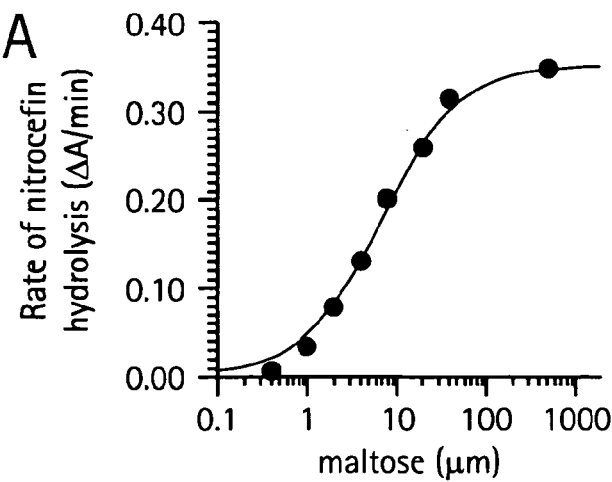
FIG. 5 (A-C) shows three graphs illustrating the properties of MBP-BLA switches. (A) shows dose-dependent response. The rate of beta-lactam hydrolysis as a function of maltose (dots) follows the maltose-binding isotherm (blue). (B) shows turning the switch MBP317-347 on and off using competing ligands. Initially, in the absence of any ligand, the rate of beta-lactam hydrolysis catalyzed by the switch is low. At about 5 minutes, maltose is added and the enzyme activity of the switch is turned on. At about 10 minutes, an excess of beta-cyclodextrin is added. This replaces maltose in the binding site and turns the enzyme activity of the switch off. At about 16 minutes, an excess of maltose is added which replaces beta-cyclodextrin and turns the enzyme activity of the switch back on. (C) shows switches function in live cells. The minimum inhibitory concentration (MIC) of the beta-lactam antibiotic ampicillin is not affect by maltose in *E. coli* cells expressing MBP or BLA (separately). In contrast, the MIC for cells expressing switch MBP317-347 is 16-fold higher in the presence of maltose than in the absence of maltose.
Figure 5B:
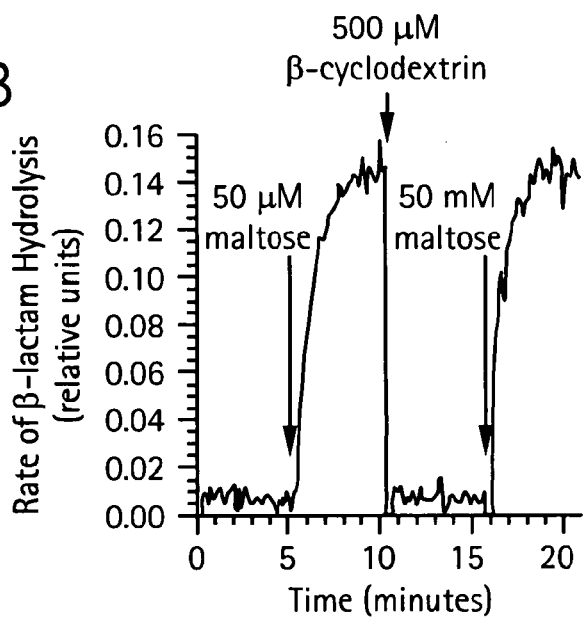

Accordingly, the data presented herein demonstrate that these switches have potential application in biomedicine and basic science. In particular, the methodology can create enzymatic activity that is conditional upon the presence of (and concentration of) a ligand unrelated to the enzyme in question. The level of activation in the presence of the desired ligand can be as high as 600-fold (6). The activation specificity is identical to the ligand specificity of the original ligand-binding protein (i.e. only in the presence of the desired ligand is the enzyme activated (6, 7). The enzyme activity responds to the ligand with a dose-response type behavior (see, e.g. FIG. 5A). The enzyme activity returns to its unactivated state when the ligand is removed (i.e. the switches are reversible). This has been demonstrated by dialyzing away the activating ligand (7) as well as competing it off the switch with a non-activating ligand (see, e.g. FIG. 5B). Enzyme switches as described herein can create new phenotypes in live cells (6, 7)

Figure 5C:
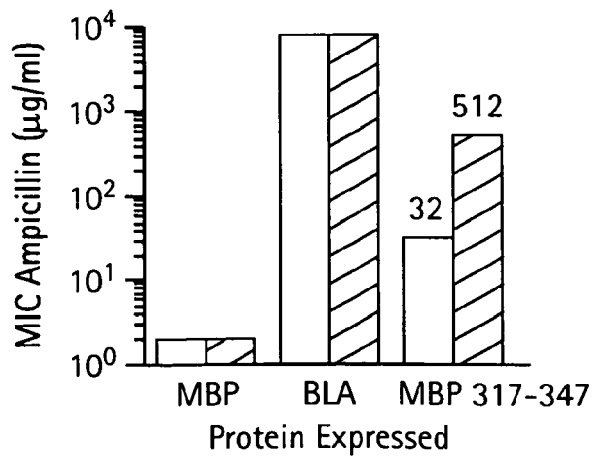

(see, e.g. FIG. 5C). This illustrates the switches ability to "rewire" the cell (in this case, antibiotic resistance is coupled to maltose concentration) and reprogram its behavior (the MBP-BLA switches gave *E. coli* a maltose-dependent resistance to beta-lactam antibiotics, see FIG. 5C). The identity of the activating ligand can be altered by mutagenesis of the ligand-binding domain followed by selection for switches that activate with the new ligand (6). The catalytic activity of the switches in the activated state can be equivalent to the original unengineered enzyme. Accordingly, the switches can be constructed without loss of activity in the active state. The described algorithm, despite sampling only a small fraction of the possible fusions of MBP and BLA6, identified a wide variety of fusions with switch properties. Note that switches with similar sequences primarily result from focused libraries at those locations (6). There are many ways to make switches between MBP and BLA making it likely there are many ways to makes switches with other proteins.

Example 2

Mechanisms of Switching

Experiments described herein are also aimed to elucidate the mechanism by which the engineered switches function. Analytical gel filtration indicates that both RG13 and MBP317-347 function as monomers (6,10) and not, for example, 3D domain-swapped dimers (70). Both RG13 and MBP317-347 have circular dichroism (CD) spectra that exhibit only minor changes upon addition of maltose, indicating that there is no gross rearrangement of secondary structure. Furthermore, the switches' CD spectra and NMR spectra approximate that of the admixture of the spectra of BLA and MBP, consistent with the structures of the switches domains being very similar to that of the parental proteins. Computational tools can be used to predict the structure of domain insertion proteins with the long-term goal of predicting switch structure.

The switching correlates with a conformational change in the MBP domain of the switch. Maltose-induced fluorescence quenching and wavelength shift in the switches described herein are much like that seen in MBP (6-8), suggesting that the MBP domain in the switches is undergoing a similar conformational change. Using mutations known to induce partially closed states in the maltose-unbound form of MBP (72, 73), the relationship between different stages of closing of the MBP domain and the catalytic activity of the BLA domain in switch RG137 have been mapped out. These studies suggest that conformational changes late in closing affect the BLA activity. In the case of switch RG13, there is evidence that the rate-determining step in NCF hydrolysis catalyzed by RG13 in the absence of maltose is deacylation of the acyl-intermediate (9). However, in the presence of maltose, the rate-determining step is not deacylation. This hypothesis is supported by recent NMR data on RG13 which is consistent with E166 in the BLA domain (the residue involved in deacylation) is displace from its normal position in the absence but not the presence of maltose. This provides evidence for a model of RG13 switching in which conformational changes late in the hinge bending motion in the MBP domain (from open to closed) modulate the relative rates of acylation and deacylation (9).

Example 3

$Zn^{2+}$ is a Negative Effector of RG13-Ligand Binding and Allostery can Emerge Simultaneously How heterotropic allostery originates is an unanswered question. The evolution of such allosteric sites must be more difficult than the evolution of non-allosteric ligand binding sites, since allosteric sites require both affinity for the intended effector and functional coupling between the effector-binding site and the active site. Experimental evidence supports a counter-intuitive model for the evolution of heterotropic allosteric effects in which effector-binding and allosteric signaling emerge simultaneously (10).

In the process of trying to convert the maltose-activated beta-lactamase switch RG13 into one that was $Zn^{2+}$ activated, it was surprisingly found that $Zn^{2+}$ already was a noncompetitive, allosteric inhibitor of RG13 that completely turned off enzyme activity. This is surprising since wild type BLA enzyme activity is not modulated by $Zn^{2+}$ and neither MBP nor BLA bind $Zn^{2+}$. The experiments described herein illustrate that new functions can emerge from domain insertion that are unexpected based on the properties of the parental proteins. Furthermore RG13, though identified from a combinatorial library, did not undergo selection for $Zn^{2+}$ regulated beta-lactamase activity. Accordingly, it is possible that the same changes that result in the ability to bind a new ligand may predispose the mutant protein to exhibit allosteric effects involving that ligand.

Example 4

Positive and Negative Selections for Cytosine Deaminase Activity

Positive and negative selections have been established for cytosine deaminase activity. In further preferred embodiments of the present invention described herein, switches will be identified that can convert 5FC to 5FU only in the presence of HIF 1a using these selections performed in a two-tier fashion. The experiments described here make use of an auxotrophic strain, GIA39 (CGSC #5594), which lacks cytosine deaminase activity. The positive selection is growth on uracil-free media minimal media in the presence of cytosine (0.267 mg/ml). Cells lacking CD cannot produce uracil and cannot grow, as shown in FIG. 6A. Cells with CD activity can grow because CD converts cytosine to uracil. The negative selection is growth of GIA39 on minimal media in the presence of 5FC (50 μg/ml) and uracil (1.5 μg/ml). Cells with CD activity convert 5FC to 5FU, which is toxic to the bacteria. Thus, only cells that lack CD activity will grow (FIG. 6A).

Example 5

Expression and Interaction of HIF-1a and the CH1 Domain of p300

The C-TAD domain of HIF-1 a (referred to as "HIF-1a" herein) is a short, 40 amino acid domain consisting of a helix-loop-helix (62). This domain will be used to trigger switches in the library selection process. The switches sensing domain will be the CH1 domain of p300. These two minimal maintain a high level of affinity and have been demonstrated by Freeman and coworkers to be co-expressed and co-purified in *E. coli* (62, 65). Because this interaction in *E. coli* is key to the selection process, the expression and interaction of these two domains has been verified using the expression system in *E. coli*. HIF-1 a was fused to the C-terminus of glutathione S-transferase (GST) and coexpressed with the CH1 domain. Purification of the GST-HIF-1 a using glutathione agarose beads resulted in bands at the expected size of GST-HIF-1 a and CH1, verifying the interaction when both proteins are expressed in *E. coli* (see FIG. 6B). The band migrating at the size of CH1 was not seen if GST was expressed instead of GST-HI F-1 a or if CH1 was not expressed with GST-HIF-1 a.

Example 6

Construction of Protein Switches 3 and 59 that Confer Sensitivity to Cells to the Prodrug 5-FC The algorithm that has been described for creating switches does not depend on knowledge of the structure of the two proteins to be fused nor does it depend on understanding the mechanism by which switching is achieved. Thus, in theory, any two genes encoding the prerequisite input and output functions for a desired switch could be recombined using our method resulting in a library containing members that behave as switches. However, the ability to rapidly and efficiently identify the rare proteins that behave as switches in this library is key for the success of the approach. As described herein, the proteins chosen for the 'proof-of-principle' type experiments (MBP and BLA) were chosen with ease of identification of switches in mind. As described herein, a family of MBP-BLA switches was created that exhibited the properties desired of switches for therapeutic protein and sensing applications. A next set of experiments describes such applications. The next step is to demonstrate that switches can be built for such applications. For example, the next set of experiments describes switches that activate a prodrug only in the presence of a protein that is a marker for cancer.

In particular examples, the present invention describes, in part, two switch protein genes that make cells, and in particular *E. coli* cells sensitive to the prodrug 5-fluorocytosine (5-FC) but only when the hypoxia inducible factor-1alpha (HIF-1a) protein is produced.

A commonly used enzyme prodrug pair for GDEPT is cytosine deaminase (CD) and 5-fluorocytosine (5FC). Cytosine deaminase (CD) is an enzyme that converts the non-cytotoxic antifungal drug 5FC to 5-fluorouracil (5FU)—an FDA-approved, widely-used chemotherapy agent for treating various cancers.

Cytosine deaminase activity is not endogenous to human cells, thus 5FC is well tolerated. Once 5FC is deamidated by CD to 5FU, the analogue is anabolized to 5-FdUMP by cellular enzymes and acts as an irreversible inhibitor of thymidylate synthase, thereby preventing DNA replication and blocking dTTP synthesis. A key advantage of 5FC/CD combination is that not all tumor cells need to be transduced with the suicide gene provided the toxic drug produced in a transduced cell is released and taken up by neighboring untransduced cells. This is known as the bystander effect. Unlike the product of another common enzyme/prodrug pair for GDEPT (HSV thymidine kinase and ganciclovir), 5FU can penetrate tumor cells by passive diffusion and more effectively exhibits the bystander effect. Another advantage is that since the enzyme is produced inside the cell, it is much less likely to generate an immune response and neutralizing antibodies and any immune response will be target to the tumor (35). Finally, 5FU has radiosensitizing properties; thus radiation regimens can be used to augment treatment (36).

CD from *E. coli* (bCD) is a hexamer of 60 kDa subunits. It has been successfully used in gene therapy in a variety of animal tumor models and has been under investigation for the treatment of human cancers (37,35). However, the limiting factors for success are transfection efficiency of the CD gene and the activity of the enzyme (38). Variants of bCD with improved catalytic activity have been described (38, 39).

Yeast CD (yCD) is a homodimer composed of 17.5 kDa subunits and has been shown to be a better enzyme at converting 5FC to 5FU (40), but it has lower thermostability. However, mutants of yCD with improved thermostability have been identified that have improved its stability and performance in cell culture assays and in animal models (41, 42). The yCD/5FC system has been tested in numerous animal models and is currently being evaluated in several clinical trials (42).

Figure 7:
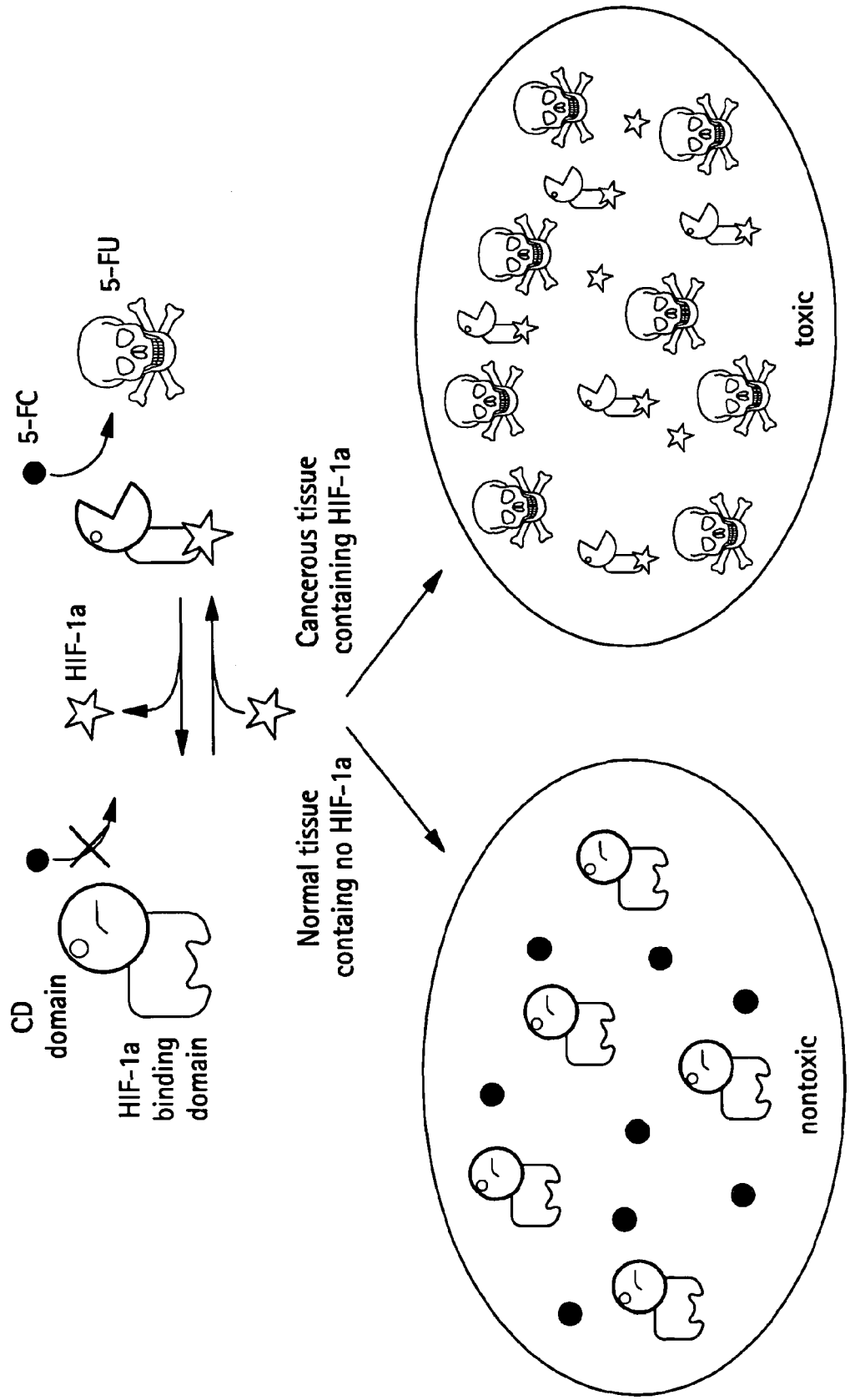
FIG. 7 is a diagram that shows a schematic mode of action of exemplary protein switches 3 and 59 in normal (left) and cancer (right) cells. The protein switch is activated in cancer cells by HIF1-a and then the prodrug (5FC) is converted into the anticancer drug (5FU). The protein switches will not be activated in normal cells because of the very low levels of HIF1-a and the prodrug will remain nontoxic.

In certain preferred embodiments, the present invention describes the use of hypoxia-inducible factor 1a (HIF-1a) as the activating signal to turn on the switch's prodrug-activating activity. HIF-1a has long been regarded as a cancer-specific marker, and tumor initiation and progression have been directly linked to HIF-1a (43-46). HIF-1a is involved in oxygen sensing within all cells and is a subunit of the heterodimeric transcription activator HIF-1 (47-49). HIF-1a is constitutively expressed but is regulated such that its level in normal cells under normal oxygen tension conditions (normoxia) is virtually undetectable. However, HIF-1a levels increase dramatically by two independent mechanisms: (1) under low oxygen conditions (hypoxia) and (2) as a result of gain-of-function mutations in tumor suppressor genes. This is shown in a schematic in FIG. 7.

Under normoxia, HIF-1 a is rapidly degraded by the 26S proteasome via the ubiquitin-proteasome pathway (50, 51). HIF-1a degradation is dependent upon the presence of oxygen, which is used to hydroxylate three residues (Pro402, Pro564 and Asp803) within HIF-1 a, thus HIP-1a's role as a cellular oxygen sensor (52, 53). Proline hydroxylation in HIF-1a is recognized by the von Hippel-Lindau tumor suppressor protein (VHL) and the protein is targeted for degradation. Its half-life within a normoxic cell is on the order of 1 to 4 minutes (53, 54) making its half-life the shortest of any known protein (55). As a result, under normoxic conditions HI F-1 a turnover is so instantaneous that HI F-1 a is virtually undetectable in normal cells. Asp803 hydroxylation prevents association with the CH 1 domain of p30056, an interaction necessary for translocation to the nucleus and the activation of HIP-1a-dependent genes.

As oxygen becomes rate limiting, hydroxylation of the prolines diminishes and HIF1 a accumulates in the cytoplasm. Hydroxylation of Asp803 is also inhibited under hypoxic conditions, allowing HIF-1a to associate with the CH1 domain of p300. HIF-1a bound to the p300/CBP protein complex translocates to the nucleus where it dimerizes with HIF-113 to become holo HIF-155. Here, holo HIF-1 drives the transcription of over 100 genes directly (57) and nearly a thousand indirectly (55). Adaptation to regions of hypoxia within a solid tumor is critical to tumor progression (58), and is innately associated with the overexpression of HIF-1 a. The near universality of hypoxia in human tumors and the HIF pathway's central role in adaptation to hypoxia indicates that HIF-1a is an excellent signal for tuning on the switches that are described in the experiments herein. However, intratumoral hypoxia is not the only basis for high levels of HIF-1 a. Genetic alterations to well-known oncogenes, for example VHL, p53, EGFR and PTEN, have also been show to increase HIF-1a expression (43, 59). HIF-1 can induce a number of genes that control energy metabolism, survival and cell migration, all of which promote cancer proliferation. A recent retrospective study reviewed the role of HIF-1a in sixteen types of human cancer, encompassing data from over 2,100 patients (60). This shows that HIF-1 a overexpression is observed in most human cancers including lung, breast, prostate and colon cancer but not in the corresponding normal tissue. For example over 80% of cancerous tissue from prostate cancer stained strongly positive for HIF-1 a, while HIF-1 a was not detected in their normal prostate tissue.

Many groups are searching for ways to disrupt the HIF pathway as a potential route to cancer therapies, with promising results (61). However, the present invention seeks to exploit HIF-1 a overexpression in cancer as a signal to produce a cancer therapeutic only in cancer cells.

Figure 2:
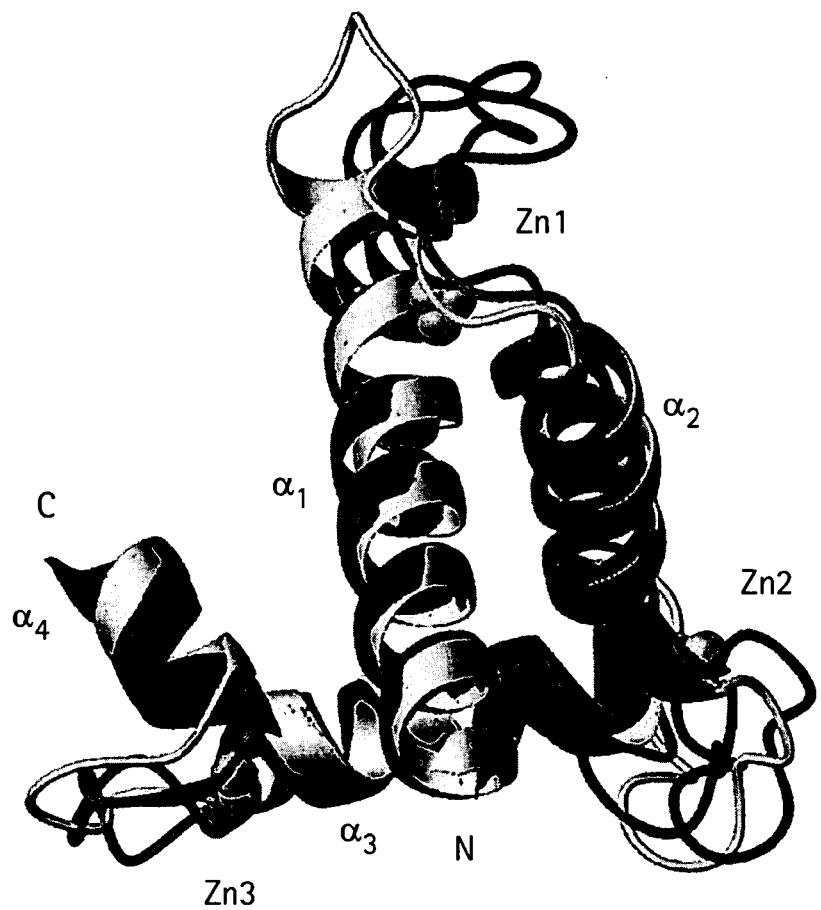
FIG. 2 is an illustration showing superposition of the ribbon structures of the p300 CH1 domain when free, complexed with HIF-1a and complexed with CITED2.

The present experiments make use of the CH1 domain (also known as TAZ1) of p300 as the input domain (i.e. the "cancer-sensing" domain) of the switch. Overexpressed HIF-1 a is specifically bound by the CH1 domain of p300/CBP protein complex and translocated into the nucleus where it dimerizes with HI F-113 to become holo HIF-1 and activate a large number of genes (55). Under normoxia, hydroxylation of Asn803 sterically interferes with binding to the CH1 domain of p30062. The CH1 domain from p300 is composed of 100 amino acids, which are arranged as three a-helices (62). This is shown in FIG. 2. The C-TAD domain of HIF-1a and the CH1 domain of p300/CBP (i.e. only the CH1 domain) were sufficient to maintain a strong interaction between the two proteins and the two have been co-crystallized (62-64). The C-TAD domain of HIF-1a (referred to as "HIF-1a" herein) is a short, 40 amino acid domain consisting of a helix-loop-helix (62). These two minimal domains maintain a high level of affinity (Kd of 120 nM) and can be co-expressed and co-purified in E. coli (62, 63, 65) and this has also been verified by the present inventors. NMR studies indicate that the CH1 domain undergoes some conformational changes upon binding HIF-1 a (see FIG. 2) (66). Conformational changes upon ligand binding were correlated with switching with the MBP-BLA switches and are presumed to facilitate the creation of switches because this change can effect the conformation of the enzyme domain. The switches described herein are unlikely to cause the undesirable accumulation of HIF-1 a in normal cells because the hydroxylation of Asp803 will prevent interaction of HIF-1 a with the CH1 domain of our switches.

There are other known transcription factors that bind to CH1, such as CITED2, p53 and Tall. It will be important for switch specificity that none of these other transcription factors activate the switch. However, there are several reasons to believe that this can be achieved. (1) These transcription factors do not share any obvious sequence similarity; thus, it is likely they bind to different surfaces of CH1 (65). The MBP-BLA switches could distinguish between different sugars, even when binding at similar sites. Maltose was an agonist and p-cyclodextrin is an antagonist of the best switch MBP317-347 (6). (2) Many of the other transcription factors known to bind CH1 are also cancer markers (e.g. p53); thus, activation of the switches by these other factors may actually be desirable (3). Among the transcription factors, only HIF-1a (62) and CITED2 (65) have been shown through structural studies to form a complex with an isolated CH1 domain; thus, it is possible that the other transcription factors require other motifs from p300 in addition to CH1 in order to form a complex. If this is true, then they will be unable to bind and activate the switches. For example, p53 has low affinity for the CH1 domain in isolation (Kd=100 RM)67. (4) HI F-1 a and CITED2 bind mostly different surfaces on CH1 (65) and induce different conformational changes in CH1 (see FIG. 2); thus, it should be possible to distinguish these binding events.

Protein switches 3 and 59 are hybrid proteins composed of yeast cytosine deaminase (yCD) and the CH1 domain of the human p300 protein (CH1). The CH1 domain has a high affinity for HIF-1a (89), which is overexpressed in many types of cancer (90). yCD is an enzyme that can convert the innocuous 5-FC prodrug into the toxic 5-fluorouracil (5-FU).

The experiments described herein describe the creation of hybrids whose yCD activity was high only in the presence of HIF-1a. Hybrids having this phenotype could then be used to selectively kill tumor cells, for example as shown in the schematic shown in FIG. 1. Normal human cells would not be affected by this treatment since HIF-1a is virtually undetectable in normal human cells. As described in the experiments herein, protein switches 3 and 59 were isolated from a combinatorial library of hybrids that were placed under selective pressure to identify those fusions in which the activity of the yCD domain in the fusion has higher activity in the presence of HIF-1a than in the absence.

Library Construction

Figure 8:
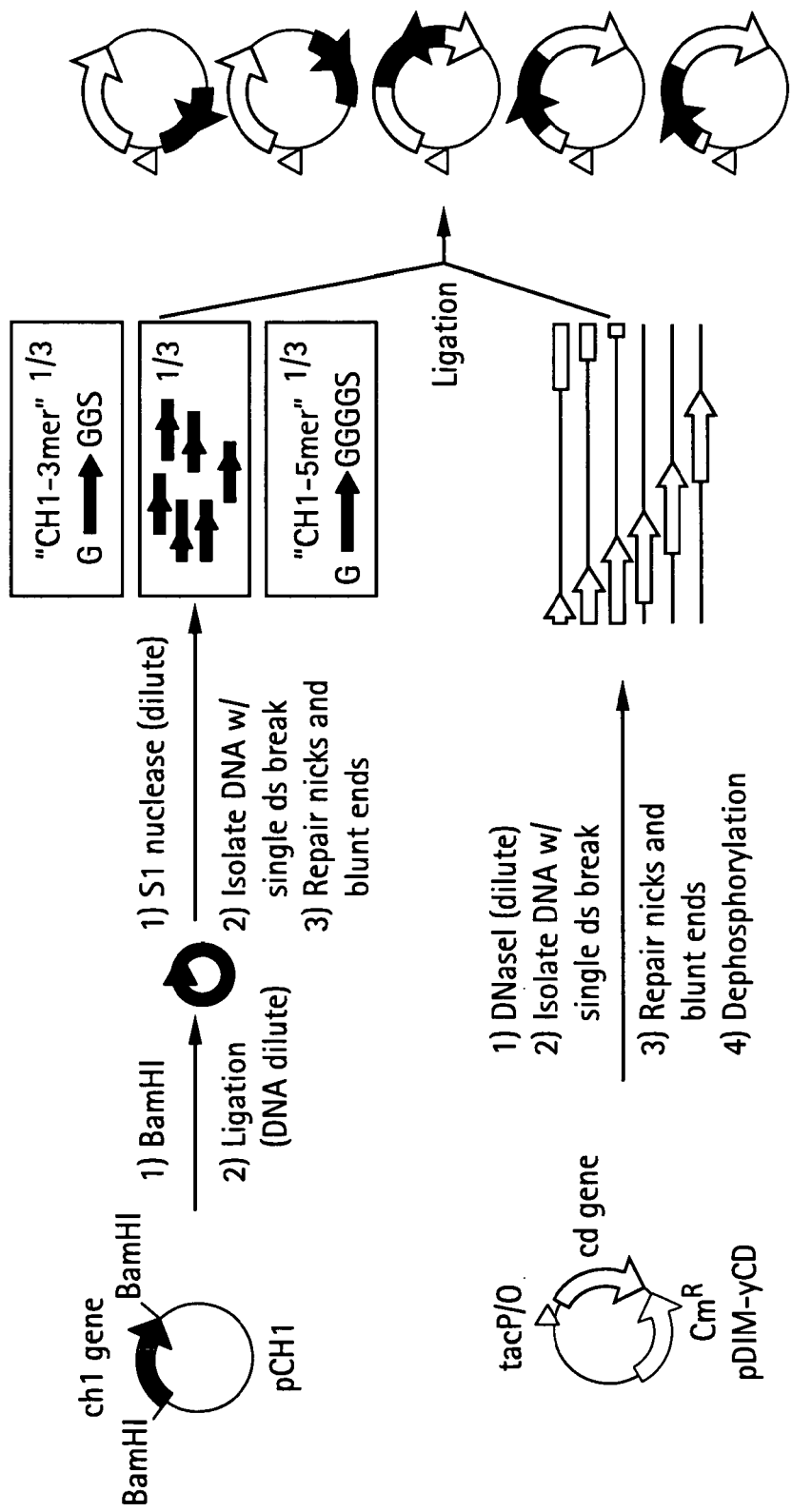
FIG. 8 is a schematic showing the random domain insertion method used to create protein switches 3 and 59. The CH1 domain inserts (cpCH1, CH1-3mer and CH1-5mer) were mixed in an equimolar ratio before they were used in the ligation mixture.

FIG. 8 shows a schematic of how libraries involving circular permutation are constructed according to certain preferred embodiments of the present invention. Table 1, shown below, summarizes the types of libraries that will be constructed.

TABLE 1

Table 1 Libraries to be constructed.

| Library number | Target domain | Insert domain | Insert domain linker (s) |
|---|---|---|---|
| 1 | yCD-triple | CH1 | none |
| 2 | yCD-triple | CH1 | N-terminal: GS C-terminal: GGS |
| 3 | yCD-triple | CH1 | N-terminal: GS C-terminal: GGGGS |
| 4 | yCD-triple | cp-CH1 | Circular permutation linker: GSGGG |
| 5 | yCD-triple | cp-CH1 | Circular permutation linker: (GSGGG)$_2$ |
| 6 | yCD-triple | cp-CH1 | Circular permutation linker: (GSGGG)$_3$ | cp refers to a circularly permuted library.

Switches have been created by two different strategies. In the first strategy, random insertions of one gene into another are used to find useful insertion sites for switches (8). These switches are then used as starting points for an iterative method (involving circular permutation) for making improved switches (8). In the second strategy, circular permutation is incorporated from the start. Libraries of a randomly circularly permuted gene are randomly inserted into the second gene'. Both of these strategies will be applied in parallel.

In both strategies linkers are used at the ends of the CH1 domain, either to serve as linkers for fusion to yCD (Libraries 1-3) or to serve as linkers for the circular permutation of CH1. In the structure of the CH1 domain bound to HIF-1a the N- and C-termini on average are pointing somewhat away from each other but the set of NMR structures show a lot of variability and flexibility at both termini (62). Thus it is uncertain what the correct linker length should be. In fact, different linker lengths may be appropriate for different fusions with yCD. Thus, several libraries with different linker lengths are constructed and tested. A flexible GSGG linker was used to construct MBP-BLA switches (8) and replacement of the more inflexible DKS linker with the GSGG linker in the best MBP-BLA switch only slightly reduced switching activity. In other words, a flexible linker between the N- and C-termini is compatible with making switches, thus the flexible linkers for the CD libraries (Table 1) will likely be successful.

Each of these libraries preferably consists of 108-107 transformants. Although the majority of members of these libraries are constructs in which the insert gene was either (1) inserted outside the target gene, (2) inserted backwards relative to direction of the target gene, or (3) inserted out of frame relative to the reading frame of the target gene, this is not a concern. First, this was also the case with the MBP-BLA libraries from which switches were successfully created. Second there is a genetic selection for switching activity from which all members of the library in a single two-tiered selection taking only two days (see next section). Finally, the population of library members with inserts in the target gene, in the right orientation and with both crossovers in-frame is still very large and will consist of approximately 104-105 unique members (6). Note that the method of creating the libraries generates deletions and tandem duplications at the site of circular permutation and insertion in addition to "perfect" circular permutations and insertions. This added level of diversity is important for creating switches (almost all MBP-BLA switches had either deletions or tandem duplications) and means that the vast majority of the $10^4$-$10^5$ are unique constructs (6). The fact that switches usually have deletions or tandem duplications that are required for switching activity illustrates the difficulty in trying to rationally design switching activity, even in the case where structural information on the individual domains is known, since it is very difficult to predict the conformation at the site of insertion—a conformation that is likely to be key to the switching activity. Tandem duplications may also serve a linker function for the fusions.

In certain particular preferred embodiments of the present invention, yCD containing the A23L/V108I/I140L stabilizing mutations (92) was cloned into a pDIM-C8 vector, which has chloramphenicol resistance. Microgram quantities of this plasmid were isolated, and then digested with DNaseI using a method described by Guntas and coworkers (91). DNaseI will randomly cut dsDNA. Plasmid DNA with a random double-stranded break was isolated using gel electrophoresis (FIG. 2). The singly cut DNA was repaired and blunted using T4 DNA ligase and T4 DNA polymerase, resulting in randomly cut yCD plasmid DNA. Singly cut and repaired yCD plasmids DNA were again isolated using gel electrophoresis and used in a ligation reaction with CH1 inserts. Three types of CH1 domain inserts were prepared. Two inserts were described as direct inserts and appended on the 3' end of the gene with DNA encoding a "GGS" peptide linker ("3mer") or a "GGGGS" peptide linker ("5mer"). Another CH1 domain insert was prepared using the circular permutation method shown in FIG. 8. The gene coding for the CH1 domain has a segment of DNA appended coding for a (GSGGG)3 peptide linker designed to join together the N- and C-termini of the CH1 domain. The appended CH1 gene was cyclized and randomly circularly permuted using S1 nuclease before insertion into the cut CD plasmids. To accomplish this, the CH1 gene was excised from its plasmid and the ends of the gene ligated together. S1 nuclease was added (2.5 U/ug) to make single double-stranded cuts within the cyclized CH1 gene, and the singly cut genes were isolated using gel electrophoresis. The isolated, linear CH1 genes were repaired and blunted as described above in preparation for the ligation reaction.

Ligation Reaction and Electroporation in *E. coli*

An initial test ligation reaction consisted of 100 ng of yCD plasmid DNA and the CH1 inserts in a 1:5 molar ratio, (yCD:CH1). The CH1 inserts were mixed together in an equimolar ratio before addition to the ligation reaction. Ligated plasmids were electroporated into DH5α *E. coli* cells and plated on LB agar containing chloramphenicol. The resulting colonies were counted to estimate the library size and then swept to recover the ligated plasmids. The isolated plasmids were digested to assess the percentage of the library containing a CH1 domain insertion into the yCD gene. The number of transformants was $2.4 \times 10^6$ of which 20-25% had an insertion of the CH1 DNA in the yCD DNA.

A larger ligation reaction was prepared in the same ratio, but using 500 ng of yCD plasmid DNA. The ligation mixture was electroporated into DH5α *E. coli* cells using the same method and plated on LB agar in a 24.5×24.5 cm Bio-Assay dish containing chloramphenicol. Another LB agar plate containing chloramphenicol was used to estimate the size of this larger library. The number of transformants was $8.6 \times 10^6$ of which 20-25% had an insertion of the CH1 DNA in the yCD DNA. The library cells were recovered from the plate and aliquoted into 14 250 µL aliquots. One aliquot was used to prep library plasmids that were utilized to transfect an auxotrophic strain of *E. coli*, GIA39 (CGSC #5594). GIA39 is an auxotroph for uracil when plated on minimal media. These cells cannot grow on minimal media unless it is supplemented with uracil, or unless the cells are harboring a plasmid that has an active CD enzyme and the media is supplemented with cytosine. The CD protein can convert the cytosine to uracil and the cells will be able to grow. GIA39 cells were transformed with the library plasmid and plated on LB agar containing chloramphenicol. The cells were recovered from the plate and aliquoted as before. The GIA39 cells harboring library plasmids were used in the selection scheme described below.

Library Selection Scheme

Minimal media was used in the selection schemes and was based on a product mixture described by Sigma. For 1L it containing 20 g of Select Agar (Sigma# A5054), 6.7 g of Yeast nitrogen base without amino acids (Sigma #Y0626), 1.92 g of Yeast synthetic drop-out without uracil (Sigma #Y1501), glucose to 2%, 1 mM IPTG and 50 µg/mL of chloramphenicol. For "negative" selection media, the above media was supplemented with 75 µg/mL or 25 µg/mL of 5FC and 1 µg/mL of uracil. For "positive" selection media, supplementation was with 25 µg/mL of cytosine, 1 mM arabinose and 100 µg/mL of ampicillin. Each Bio-Assay dish contained 250 mL of selection media and each standard Petri dish contained 25 mL of media.

The selection scheme was developed to isolate library members whose CD activity is "off" in the absence of HIF-1a but "on" in the presence of HIF-1a. Livingston and coworkers showed that a GST fusion of HIF-1a is able to bind to the CH1 domain when it is co-expressed on a separate vector in *E. coli* (89). A GST-HIF-1a fusion was created that is under the control of the arabinose promoter on a plasmid that can coexist with the pDIM-C8 library plasmids. This "HIF-1a plasmid" is a variation of the pGEX plasmid and has ampicillin resistance. During selections, this HIF-1a plasmid will either be present to produce HIF-1a and activate the hybrid protein switches, or absent to avoid any production of HIF-1a.

During the negative selection, no HIF-1a plasmid was present in the cells. Thus, hybrids that are active in the absence of HIF-1a will convert the 5FC into 5FU and kill the cell. But, hybrids that are not active in the absence of HIF-1a will be able to use the minimal amount of uracil provided and grow to form colonies. The negative selection was performed twice in succession using the Bio-Assay dish size plates (2 plates each time with about 600,000 cells plated on each plate). The first time the negative selection media contained 75 µg/mL 5FC. The colonies that grew on this plated were recovered and then underwent a second negative selection to help ensure that any pDIM-C8 plasmids encoding a wild-type yCD were removed from the library. The second negative selection was performed the same as the first except that 25 µg/mL of 5FC was used. The cells that survived the second negative selection were harvested and then aliquoted. One aliquot was used to isolate library plasmids that were used in the positive selection that followed.

Library plasmids isolated from the negative selection were transformed into GIA39 cells that harbored the HIF-1a plasmid. After the electroporation, the GIA39 cells were plated on LB agar containing both ampicillin and chloramphenicol to ensure that the cells contained both the pDIM-C8 library plasmids and the HIF-1a plasmid. These cells were recovered from the plate and aliquoted. These cells were then plated on positive selection media containing cytosine and arabinose (two Bio-Assay plates with about 600,000 cells plated on each plate). "Positive selection" media contained cytosine, as well as arabinose to induce HIF-1a expression. If hybrids were active in the presence of HIF-1a, they could convert cytosine into uracil and the cells will grow. Colonies that formed on positive selection plates were screened as described below.

Selection Results and Characterization

A total of 0.008% of the CFUs plated (CFUs determined on minimal plates supplemented with uracil) formed colonies on the positive selection plates. These 99 colonies were screened for those which harbored a pDIM-C8 plasmid that contained a CH1 insert in the yCD gene using colony PCR and electrophoresis to observe a shifted band. Eight of the colonies screened had a shifted band that corresponded to a yCD-CH1 hybrid and these genes were sequenced. One of these genes was out of frame and was discarded. The remaining seven comprised five different sequences with one clone (91) being found three times. These five genes were tested under the positive and negative selections to ensure they conferred growth under both conditions. Two of the five genes, encoding protein switch 3 and 59, behaved as desired and grew on both the positive and negative selection plates. Switch 3 resulted from the 3mer CH1 insert and switch 59 from the circularly permuted CH1 insert. Both contained the CH1 domain inserted in almost exactly the same location near the beginning of the yCD gene. DNA and protein sequences of the switch genes and proteins are provided below.

Verification that the Switch Genes Make E. coli Sensitive to 5FC but Only when HIF1-a is Produced This experiment confirmed that the switch genes conferred sensitivity to 5FC depends on induction of expression of HIF1-a (see Table 2, below).

TABLE 2

| Protein being expressed from pDIM-C8 | Growth on "negative selection" minimal plates supplemented with 75 µg/ml5FC | | | |
|---|---|---|---|---|
| | w/o HIF1-a plasmid | | w/ HIF1-a plasmid | |
| | No arabinose | 1 mM arabinose | No arabinose | 1 mM arabinose |
| MBP (− control) | + | + | nd | nd |
| yCD (+ control) | − | − | − | − |
| Switch #3 | + | + | + | − |
| Switch #59 | + | + | + | − |

+ = growth
− = no growth
MBP = maltose binding protein
yCD = yeast cytosine deaminase containing the A23L/V108I/I140L mutations
nd = not determined Cells harboring the switch genes in pDIM-C8 or cells with the same plasmid together with the HIF1-a plasmid were plated on minimal media plates supplemented with 5FC (i.e. the negative selection conditions). These plates either did or did not contain arabinose. The desired result would be that cells harboring the switch genes would grow under all conditions except when they also harbored the HIF-1a plasmid AND the media was supplemented with arabinose to induce HIF 1-a expression. This is exactly the result obtained (as shown in Table 1). As a positive control, yCD was expressed from the pDIMC8 plasmid, which had the expected behavior of making the cells susceptible to 5FC under all conditions.

The negative control (maltose binding protein expressed from pDIM-C8) grows whether or not arabinose is added as expected. This experiment is key because it establishes that the switch genes make the cells susceptible to 5FC but only when HIF1-a is produced. One reason is because HIF-1a binds to the switch and increases the ability of the switch to convert 5FC to 5FU. This is a desired activity for the switch genes to have in eukaryotic cells for therapeutic applications.

Repeating the Selection

As further evidence of the approach described here, the selection process was repeated on the library exactly as before except that in the second negative selection, 50 µg/mL 5FC was used instead of 25 µg/mL. After the positive selection, screening of the 26 colonies resulted in the identification of a gene conferring the desired switching property. The DNA sequence of this gene was the same as switch 59. Independent isolation of the same sequence in two separate experiments (recall that switch 3 was isolated 3 times in the first selection experiment) is strong evidence that these genes were not isolated for spurious or stochastic reasons.

The DNA and protein sequences of switches 3 and 59 as represented by SEQ ID NOs 1-4 are shown below:

```
SEQ ID NO: 3:
Switch 3, DNA sequence
ATGGTGACAGGGGGAATGGCAAGCGGCGATCCGGAAAAACGTAAACTG
ATCCAGCAGCAGCTGGTGCTGCTGCTGCATGCTCACAAATGTCAGCGT
CGTGAACAGGCAAACGGCGAAGTACGTCAGTGCAACCTGCCGCACTGC
CGTACAATGAAAAATGTACTGAACCACATGACCCACTGCCAGAGCGGT
AAAAGCTGCCAGGTAGCTCACTGCGCATCTTCTCGCCAGATTATCTCT
CACTGGAAAAACTGCACCCGTCACGATTGCCCGGTTTGCTTGCCGCTC
AAGAACGCTGGTGGCTCGAAGTGGGATCAGAAGGGTATGGACATTGCC
TATGAGGAGGCGCTCTTAGGTTACAAAGAGGGTGGTGTTCCTATTGGC
GGATGTCTTATCAATAACAAAGACGGAAGTGTTCTCGGTCGTGGTCAC
AACATGAGATTTCAAAAGGGATCCGCCACACTACATGGTGAGATCTCC
ACTTTGGAAAACTGTGGGAGATTAGAGGGCAAAGTGTACAAAGATACC
ACTTTGTATACGACGCTGTCTCCATGCGACATGTGTACAGGTGCCATC
ATCATGTATGGTATTCCACGCTGTGTTATCGGTGAGAACGTTAATTTC
AAAAGTAAGGGCGAGAAATATTTACAAACTAGAGGTCACGAGGTTGTT
GTTGTTGACGATGAGAGGTGTAAAAAGCTCATGAAACAATTTATCGAT
GAAAGACCTCAGGATTGGTTTGAAGATATTGGTGAGTAG SEQ ID NO: 1
Switch 3, Protein sequence (segment origination
from CH1 in red)
MVTGGMAS**GDPEKRKLIQQQLVLLLHAHKCQRREQANGEVRQCNLPHC
RTMKNVLNHMHTHCQSGKSCQVAHCASSRQIISHWKNCTRHDCPVCLPL
KNAGGS**KWDQKGMDIAYEEALLGYKEGGVPIGGCLINNKDGSVLGRGH
NMRFQKGSATLHGEISTLENCGRLEGKVYKDTTLYTTLSPCDMCTGAI
IMYGIPRCVIGENVNFKSKGEKYLQTRGHEVVVVDDERCKKLMKQFID
ERPQDWFEDIGE SEQ ID NO: 4
Switch 59, DNA sequence
ATGGTGACAGGGGGAATGGCAAGCGATCCGGAAAAACGTAAACTGATC
CAGCAGCAGCTGGTGCTGCTGCTGCATGCTCACAAATGTCAGCGTCGT
GAACAGGCAAACGGCGAAGTACGTCAGTGCAACCTGCCGCACTGCCGT
ACAATGAAAAATGTACTGAACCACATGACCCACTGCCAGAGCGGTAAA
AGCTGCCAGGTAGCTCACTGCGCATCTTCTCGCCAGATTATCTCTCAC
TGGAAAAACTGCACCCGTCACGATTGCCCGGTTTGCTTGCCGCTCAAG
AACGCTGGTGGCTGGGATCAGAAGGGTATGGACATTGCCTATGAGGAG
GCGCTCTTAGGTTACAAAGAGGGTGGTGTTCCTATTGGCGGATGTCTT
ATCAATAACAAAGACGGAAGTGTTCTCGGTCGTGGTCACAACATGAGA
TTTCAAAAGGGATCCGCCACACTACATGGTGAGATCTCCACTTTGGAA
AACTGTGGGAGATTAGAGGGCAAAGTGTACAAAGATACCACTTTGTAT
ACGACGCTGTCTCCATGCGACATGTGTACAGGTGCCATCATCATGTAT
GGTATTCCACGCTGTGTTATCGGTGAGAACGTTAATTTCAAAAGTAAG
GGCGAGAAATATTTACAAACTAGAGGTCACGAGGTTGTTGTTGTTGAC
GATGAGAGGTGTAAAAAGCTCATGAAACAATTTATCGATGAAAGACCT
CAGGATTGGTTTGAAGATATTGGTGAGTAG
```

-continued

SEQ ID NO: 2
Switch 59, Protein sequence (segment origination
from CH1 in red)
MVTGGMAS**DPEKRKLIQQQLVLLLHAHKCQRREQANGEVRQCNLPHC
RTMKNVLNHMTHCQSGKSCQVAHCASSRQIISHWKNCTRHDCPVCLPL
KNAGG**WDQKGMDIAYEEALLGYKEGGVPIGGCLINNKDGSVLGRGHNM
RFQKGSATLHGEISTLENCGRLEGKVYKDTTLYTTLSPCDMCTGAIIM
YGIPRCVIGENVNFKSKGEKYLQTRGHEVVVVDDERCKKLMKQFIDER
PQDWFEDIGE Iterative Library Construction.

The best MBP-BLA switches were identified through an iterative process in which focused libraries based on identified switches were constructed (6). This iterative process for finding improved switches is based on the hypothesis that sites for circular permutation or domain insertion in existing switches will be more likely to create improved switches than sites chosen at random. In certain preferred embodiments, this iterative process may be used to create improved switches. This process has been used in the past to progress from a switch with only 1.4-fold increase in catalytic activity in the presence of ligand to one with a 600-fold increase (6). The two-tiered genetic selection described herein will greatly facilitate this iteration.

Example 7

Biochemical and Biophysical Characterization of the Switches In Vitro

Careful in vitro characterization of switches will identify the switches with the best properties (e.g. largest difference in prodrug-activating activity, most active fusion for producing, for example, 5FU, appropriate affinity and specificity for HIF-1 a, appropriate stability) to be carried forward for efficacy in live cells, as described herein. Also, testing the efficacy in live cells of switches with different known affinities for HIF-1 a will be useful in identifying the appropriate affinity for HIF-1 a.

Library members identified as switches are be sequenced to identify the exact gene fusions resulting in switching activity. The best switches (based on preliminary characterization) are be fused to GST and purified using agarose-glutathione beads. The switch domain is then be cleaved from the GST domain using precision protease (for example, as demonstrated with GST-yCD fusions). The switches enzymatic activity and stability is then determined in the absence and presence of purified HIF-1 a and CITED2 (to test for specificity). These characterizations are carried out at physiological temperature (37° C.). Purified HIF-1 a will be produced in E. coli as a GST fusion with a precision protease site, and purified in an analogous manner to the purification of the switches.

As described herein, the CH1 domain of p300 is at least partially responsible for the interaction of p300 with other transcription factors. In preferred embodiments, switches are preferred that are specifically activated by HIF-1 a and not these other transcription factors. Experiments can test for specificity. Since CITED2 binds to a site on CH1 that partially overlaps the HIF-1 a-binding site, CITED2 can be used as a model to test for specificity. CITED2 has been expressed as a GST fusion and shown to form a complex with the CH1 domain in E. coli (65). First GST-CITED (under an arabinose promoter) can be tested to see if it can activate the switches in vivo using positive and negative selection in a manner completely analogous to how HIF-1a's activation was verified as described herein. Switches are selected that are activated specifically by HIF-1 a. In certain cases when all switches are activated by both HIF-1 a and CITED2, these switches can still be used as described herein.

The affinity of the switches for HIF-1 a will be determined before performing detailed kinetic assays to ensure sufficient HIF-1 a is used for determining the kinetic parameters for prodrug activation in the presence of bound HIF-1 a. Preferably, an effective switch will be one with an affinity for HIF-1 a in an appropriate range. It is not certain what this range should be, since the precise concentrations of HIF-1 a in normal and cancerous cells is unknown. The dissociation constant of the CH1 domain and HIF-1 a has been measured in vitro at 25° C. to be about 120 nM (64). Since it is this interaction that leads to aberrant stimulation of gene expression in cancer cells, it is expected that HIF-1 a levels are substantially lower than 120 nM in normal cells and higher than 120 nM in cancerous cells. Accordingly, it may be predicted that switches with a Kd for HIF-1a of about 120 nM will be effective, but this may vary. A comparison of in vitro data on HIF-1a/switch affinity and live cell efficacy will help determine the appropriate HIF-1 a affinity for a switch to have efficacy in live cells.

All affinity experiments will be performed using purified protein at 37° C. in phosphate buffered saline (PBS) to obtain physiologically relevant data. Since the CH1 domain requires $Zn^{2+}$ for stability, appropriate levels of $ZnSO_4$ will be added to all assays. Since HIF-1 a will activate enzyme activity in these switches, the amount of enzyme activity will be proportional to the amount of switches with bound HIF-1 a. Thus, an apparent Kd can be determined by measuring the enzymatic activity as a function of HIF-1 a concentration. Enzyme activity will be measured using 5FC as the substrate using an established spectrophotometric assay in which readings are taken at 290 nm (the wavelength that 5FC absorbs) and 255 nm (the wavelength 5FU absorbs.

It will be verified that CITED2 does not activate the switches by performing in vitro experiments with purified switches and CITED2. The same GST-CITED2 vector for the above studies in E. coli will be used to produce CITED2, which will be cleaved off the GST using precision protease (analogous to how HIF-1 a was purified). Cytosine deaminase activity will be measured in the presence and absence of CITED2 as above. Contingent plans in the event that all switches are activated by both HIF-1 a and CITED2 are discussed herein.

All kinetic experiments will be performed using purified protein at 37° C. in PBS to obtain physiologically relevant data. The Michaelis-Menten kinetic parameters for conversion of 5FC to 5FU of switches (with and without HIF-1 a) are determined using a spectrophotometric assay as described (39). Switches are preferred that have high specific activity in the presence of HIF-1 a and low or no activity in the absence of HIF-1 a. In particular it may be possible to obtain switches with 5FC deaminase activity in the presence of HIF-1 a that is equivalent to yCD-triple activity. One of the MBP-BLA switches, had 13-lactamase activity in the maltose bound state that was equivalent to the that of the parent enzyme'; thus, this is a reasonable goal.

The above experiments will be useful particularly for characterizing switches in which there exists a difference in enzyme activity between the HIF-1a-bound and HIF-1a-unbound states. Such an allosteric mechanism is observed with the MBP-BLA created in the lab. However, MBP-BLA switches have recently been found that appear to function by ligand-induced stabilization (76) (i.e. ligand-binding stabilizes the folded state and as a result more of the switch accumulates in the presence of ligand). CH1-yCD switches that function by this mechanism, they will confer the correct phenotype to *E. coli* cells, as tested in the experiments described herein, but the purified switches may not exhibit differences in enzyme activity in vitro.

Differences in expression of the switches in the presence and absence of HIF-1a will be confirmed by Western blots. The specificity of HIF-1a's effect will be confirmed with comparisons to cells expressing CITED2 instead of HIF-1 a. It is possible that the mechanism of increased production for the phenotypic switches is specific to *E. coli*. For example, a HIF-1 a-switch interaction that prevents proteolysis in *E. coli* might not translate to human cells. However, if the phenotypic switches show significant increases in thermodynamic stability in the presence of HIF-1a, it is more likely that such switches will show HIF-1a-dependent expression differences in human cells. Thus, the effect of HIF-1a on the stability of the enzymatic activity of the switches to increasing temperature and denaturants will be determined to identify those switches in which ligand-induced thermodynamic stabilization is greatest (with comparison to CITED2). In certain preferred embodiments, it will also be desirable that phenotypic switches have near yCD-triple enzyme activity, so the Michaelis-Menten kinetic parameters of phenotypic switches will also be determined.

In certain cases, if the HIF-1a-activation of the switches is not specific (i.e. CITED2 also activates), random mutagenesis will be used on the CH1 domain of the switches to evolve switches that are specifically activated by HIF-1a. This is feasible because HIF-1a and CITED2 bind to partially overlapping but different regions of CH1 (65), so one can expect there will be mutations that will decrease affinity for CITED2 without affecting affinity for HIF-1a. This directed evolution strategy will be facilitated by the established positive and negative genetic selections. Hence, the negative selection will be used to select for switches that are no longer activated by CITED2 and the positive selection to select for switches that are still activated by HIF-1a.

Switches are preferred with the largest HIF-1a-dependence on 5FC deaminase activity. However, it is not necessary to obtain switches that function as completely on-off switches. Switches with some activity in the absence of HIF-1a may still be effective therapeutic molecules if the increase in activity in the presence of HIF-1a is significant enough. Such switches would still provide a degree of specificity of production of 5FU, which may be therapeutically significant. Any switch with activity in the presence of HIF-1a that is similar to yCD-triple activity, but shows less activity in the absence of HIF-1a would be preferred over yCD-triple for all GDEPT strategies involving CD and 5FC.

Example 8

Transfer of Functional Switches into Inducible Eukaryotic Expression Vectors and Demonstrate Selective Activity Against HIF1-a Bearing CRC and PC Cell Lines Switches successfully selected and confirmed are tested for live cell activity a next set of experiments. High levels of HIF-1a is a hallmark of many human cancers including lung, breast, prostate and colon cancer (60). In certain preferred embodiments the switches are preferably tested in colorectal cancer (CRC) and prostate caner (PC) cells for the following reasons: (1) 5FU is currently a widely use chemotherapeutic agent in the treatment of both cancers; thus, switches with the desired properties would produce a compound with proven efficacy for the treatment of these cancers and (2) current animal and clinical studies on GDEPT using CD and 5FC have focused on the treatment of colorectal cancer and prostate cancer.

Switches should in theory allow non-specific methods for delivering of the switch or switch gene to cells since only the malignant cells will have high HIF-1a expression.

Selected switches are subcloned into the eukaryotic expression vector pLenti6N5-DEST vector (Invitrogen). This vector allows for stable gene expression under the control of the CMV promoter in a wide range of mammalian cell lines. The switches are then transfected into the CRC and PC cell lines listed in Table 3, below, using Lipofectamine (Invitrogen) and neomycin (Gibco) selection.

TABLE 3

| Cell Line | Tissue Type | HIF-1α |
|---|---|---|
| Hct116 | CRC | Absent |
| Hct116 + HIF-1α | | High |
| RKO | CRC | Absent |
| RKO + HIF-1α | | High |
| DU-145 | Prostate | Absent |
| DU-145 + HIF-1α | | High |
| PC-3 | Prostate | Absent-Low |
| PC-3 + HIF-1α | | High |
| HPNE | Normal Pancreas | Absent |
| NuLi | Normal Bronchus | Absent |
| hTert-HME1 | Normal Breast | Absent |
| tHESCa | Normal Endometrium | Absent |

If stable transfectants/transductants prove difficult to construct, the molecular switches (including the NLS) will be subcloned into a tet-on vector system (pcDNA 5/TO, Invitrogen). It may also be necessary to adjust codon usage for work in the human cells. To produce appropriate positive controls, the unmodified full-length wildtype yCD-triple will be expressed from the same vector and similarly transfected. Empty vector will be transfected to provide negative controls. The level of HIF-1a in these cell lines will be quantified using the DuoSet IC ELISA assay (R&D Systems, Minneapolis).

Since hypoxia has pleomorphic effects on cells in culture (in addition to HIF-1 and downstream effects), isogenic lines will be constructed where HIF-1a cDNA is constitutively expressed. For this work, the colon cancer cell lines HCT116 and RKO will be used, since these cell lines express little if any HIF-1 under normoxic conditions (79).

Similarly, the DU145 and PC-3 prostate cancer cell lines that have little or no expression under normoxic conditions, but have documented upregulation of HIF-1 under hypoxic conditions (80-82) will be used.

"Normal" cell lines are hTert immortalized, but not transformed cell lines from normal tissues. These normal cell lines are designed to demonstrate preliminary specificity of switches. All cell lines are commercially available from the ATCC.

Alternative methods for HIF-1 induction are also possible, including use of hypoxia (83, 84) and treatment with pharmacologic agents such as $CoCl_2$, vanadate and desferoxamine. There are also alternative methods to construct isogenic pairs of cell lines by starting with parental cell lines with high normoxic HIF-1 expression and eliminating it using RNAi or gene knockout. Levels of HIF-1a in these cell lines will be quantified using the DuoSet IC ELISA assay (R&D Systems, Minneapolis).

Targeted toxicity of switch/prodrug for colon and prostate cancer cells over normal cells. The CD prodrug, 5FC (Sigma), will be titrated (3-fold serial dilutions) against the two parental CRC and PC cell lines and derivative cell lines expressing the full length normal activating enzymes. This will provide the appropriate baseline against which the switch treated cells can be interpreted.

To assess toxicity, cell counts (minimum 300 cells counted) are performed, percent trypan blue staining cells enumerated, MTT assays and assays to quantify apoptosis. MTT assays will be performed using the CELL TITER 96 Aqueous Cell Proliferation Assay (Promega), which relies on the conversion of a tetrazolium compound (MTS) to a colored formazan product by living cells. The degree of apoptosis will be assessed using the Guava MULTICASPASE Assay on a Guava Personal Cell Analysis (PCA) system (Guava Technologies, Hayward, Calif.). Briefly, cells are classified as "live", "early and mid stage apoptotic", "late-stage apoptotic" and "dead" based on two-color flow cytometry. In addition, the percent of cells undergoing apoptosis will be directly enumerated using the double stain DAPI/propidium iodide and fluorescence microscopy as previously described (85, 86). All assays will be performed in triplicate, means and standard deviations calculated. Normally distributed data will be analyzed using t-tests, while binary data, such as that generated using the Guava apoptosis assay, will be analyzed using chi-square analysis. Data will be considered significant at $p<0.01$. Switch transfected experiments below will be interpreted in the context of these control experiments, demonstrating no toxicity in the empty vector transfected cells, and complete kill in the wildtype enzyme transfected cells.

Switch transfected cells will be subsequently tested using the optimized drug concentrations determined above. Any cell line with HIF-1 a present should activate the 5FC deaminase activity of the switch and 5FU will be produced. Accordingly, cells under these conditions will have active switch enzyme activity. These cell lines will be directly challenged with 5FC, using the full-length wildtype enzyme and empty vectors as controls, and assayed for toxicity as described above. Switches may not behave as anticipated, however. If toxicity is seen in cells lacking HIF-1 a, expression may need to be reduced by using the Tet-On vector described above, and balancing switch expression levels, with appropriate basal enzyme activity. There is also the possibility that enzyme activity will be suboptimal even in the presence of HIF-1 a. This could be due to unanticipated post-translational modification that will need to engineered out, while maintaining proper enzyme activity. This will be accomplished by site-directed mutagenesis or directed evolution methodologies. One of skill in the art is duly aware of codon usage differences between E. coli and human cells.

In Vivo Experiments

In vivo experiments will be performed using xenografted tumors in nude mice, initially using the switch transfected cancer cells. These mice will be injected such that one site contains a HIF-1 a sensitive (switch-containing) cancer, while the other flank will contain the insensitive (switch lacking) isogenic partner. Following expansion, mice will be systemically treated with the prodrug. Following success in this system, xenografts from a range of mixtures of parental cancer cell lines (lacking switches) are then raised with switch containing cells. This experiment will test the hypothesis that this approach will not require that all cells within the tumor need to be transduced. The logic for this hypothesis is that these gland forming cancers that are rich in both tight junctions and gap junctions, and the latter are associated with cell-to-cell transfer of small drugs and metabolites, a phenomenon known as cooperativity (87, 88). Another related hypothesis is that local concentration of the activated drug will be high resulting in local diffusion of the activated drug to adjacent cells. Next, xenograft tumors from pure parental cells (lacking switches) will be raised in one flank and an isogenic HIF-1 a knockout isogenic control in the other flank, and the switches will be delivered in vivo using a non-integrating viral delivery system. IN certain cases, there is the possibility of smaller or more highly vascular tumors in the HIF-1a knockout tumors, and this will be corrected for. In additional embodiments, cell-specific targeting may add an additional layer of specificity. In other further embodiment, protein transduction domains (e.g. HIV-tat) might allow another option for delivery.

REFERENCES

1. De Guzman, R. N., Wojciak, J. M., Martinez-Yamout, M. A., Dyson, H. J. & Wright, P. E. CBP/p300 TAZ1 domain forms a structured scaffold for ligand binding. Biochemistry 44, 490-497 (2005).
2. Buskirk, A. R. & Liu, D. R. Creating small-molecule-dependent switches to modulate biological functions. Chem Biol 12, 151-161 (2005).
3. Dueber, J. E., Yeh, B. J., Bhattacharyya, R. P. & Lim, W. A. Rewiring cell signaling: the logic and plasticity of eukaryotic protein circuitry. Curr Opin Struct Biol 14, 690-699 (2004).
4. Ostermeier, M. Engineering allosteric protein switches by domain insertion. Protein Eng Des Sel 18, 359-364 (2005).
5. Villayerde, A. Allosteric enzymes as biosensors for molecular diagnosis. FEBS Lett 554, 169-172 (2003).
6. Guntas, G., Mansell, T., Kim, J. R. & Ostermeier, M. Directed evolution of protein switches and their application to the creation of ligand-binding proteins. Proc Natl Acad Sci USA 102, 11224-11229 (2005).
7. Guntas, G., Mitchell, S. F. & Ostermeier, M. A molecular switch created by in vitro recombination of nonhomologous genes. Chem Biol 11, 1483-1487 (2004).
8. Guntas, G. & Ostermeier, M. Creation of an allosteric enzyme by domain insertion. J Mol Biol 336, 263-273 (2004).
9. Kim, J. R. & Ostermeier, M. Modulation of effector affinity by hinge region mutations also modulates switching activity in an engineered allosteric TEM1 beta-lactamase switch. Arch Biochem Biophys 446, 44-51 (2006).
10. Liang, J., Kim, J. R., Boock, J. T., Mansell, T. J. & Ostermeier, M. Ligand binding and allostery can emerge simultaneously. Protein Sci 16, 929-937 (2007).
11. Kobayashi, H., Kaern, M., Araki, M., Chung, K., Gardner, T. S., Cantor, C. R. & Collins, J. J. Programmable cells: interfacing natural and engineered gene networks. Proc Natl Acad Sci USA 101, 8414-8419 (2004).
12. Picard, D. Posttranslational regulation of proteins by fusions to steroid-binding domains. Methods Enzymol 327, 385-401 (2000).
13. Dueber, J. E., Yeh, B. J., Chak, K. & Lim, W. A. Reprogramming control of an allosteric signaling switch through modular recombination. Science 301, 1904-1908 (2003).
14. Gossen, M., Freundlieb, S., Bender, G., Muller, G., Hillen, W. & Bujard, H. Transcriptional activation by tetracyclines in mammalian cells. Science 268, 1766-1769 (1995).
15. Spencer, D. M., Wandless, T. J., Schreiber, S. L. & Crabtree, G. R. Controlling signal transduction with synthetic ligands. Science. 262, 1019-1024. (1993).
16. Pelletier, J. N., Campbell-Valois, F. X. & Michnick, S. W. Oligomerization domain-directed reassembly of active dihydrofolate reductase from rationally designed fragments. PNAS USA 95, 12141-12146 (1998).

17. Mootz, H. D. & Muir, T. W. Protein splicing triggered by a small molecule. J Am Chem Soc 124, 9044 9045 (2002).
18. Lin, Q., Barbas, C. F., 3rd & Schultz, P. G. Small-molecule switches for zinc finger transcription factors. J AmChem Soc 125, 612-613 (2003).
19. Guo, Z., Zhou, D. & Schultz, P. G. Designing small-molecule switches for protein-protein interactions. Science. 288, 2042-2045. (2000).
20. Carter, P. & Wells, J. A. Engineering enzyme specificity by "substrate-assisted catalysis". Science, 237, 394-399. (1987).
21. Ha, J. H., Butler, J. S., Mitrea, D. M. & Loh, S, N. Modular enzyme design: regulation by mutually exclusive protein folding. J Mol Biol 357, 1058-1062 (2006).
22. Radley, T. L., Markowska, A. I., Bettinger, B. T., Ha, J. H. & Loh, S, N. Allosteric switching by mutually exclusive folding of protein domains. J Mol Biol 332, 529-536 (2003).
23. Baird, G. S., Zacharias, D. A. & Tsien, R. Y. Circular permutation and receptor insertion within green fluorescent proteins. Proc. NatL Acad Sci. U.S.A 96, 11241-11246 (1999).
24. Tucker, C. L. & Fields, S. A yeast sensor of ligand binding. Nat Biotechnol 19, 1042-1046. (2001).
25. Doi, N. & Yanagawa, H. Insertional gene fusion technology. FEBS Lett 457, 1-4 (1999).
26. Buskirk, A. R., Ong, Y. C., Gartner, Z. J. & Liu, D. R. Directed evolution of ligand dependence: Small molecule-activated protein splicing. Proc Natl Acad Sci USA 101, 10505-10510 (2004).
27. Skretas, G. & Wood, D. W. Regulation of protein activity with small-molecule-controlled inteins. Protein Sc! 14, 523-532 (2005).
28. Ataka, K. & Pieribone, V. A. A genetically targetable fluorescent probe of channel gating with rapid kinetics. Biophys J 82, 509-516. (2002).
29. Siegel, M. S. & Isacoff, E. Y. A genetically encoded optical probe of membrane voltage. Neuron 19, 735-741. (1997).
30. Collinet, B., Herve, M., Pecorari, F., Minard, P., Eder, 0. & Desmadril, M. Functionally accepted insertions of proteins within protein domains. J Biol Chem 275, 17428-17433 (2000).
31. Benouchan, M. & Colombo, B. M. Anti-angiogenic strategies for cancer therapy (Review). Int J Oncol 27, 563-571 (2005).
32. Russell, P. J. & Khatri, A. Novel gene-directed enzyme prodrug therapies against prostate cancer. Expert Opin Investig Drugs 15, 947-961 (2006).
33. Schepelmann, S. & Springer, C. J. Viral vectors for gene-directed enzyme prodrug therapy. Curr Gene Ther 6, 647-670 (2006).
34. Hacein-Bey-Abina, S., Von Kalle, C., Schmidt, M., McCormack, M. P., Wulffraat, N., Lebouch, P., Lim, A., Osborne, C. S., Pawliuk, R., Morillon, E., Sorensen, R., Forster, A., Fraser, P., Cohen, J. I., de Saint Basile, G., Alexander, I., Wintergerst, U., Frebourg, T., Aurias, A., Stoppa-Lyonnet, D., Romana, S., Radford-Weiss, I., Gross, F., Valensi, F., Delabesse, E., Macintyre, E., Sigaux, F., Soulier, J., Leiva, L. E., Wissler, M., Prinz, C., Rabbitts, T. H., Le Deist, F., Fischer, A. & Cavazzana-Calvo, M. LMO2-associated clonal T cell proliferation in two patients after gene therapy for SCID-X1. Science 302, 415-419 (2003).
35. Niculescu-Duvaz, I., Friedlos, F., Niculescu-Duvaz, D., Davies, L. & Springer, C. J. Prodrugs for antibody- and gene-directed enzyme prodrug therapies (ADEPT and GDEPT). Anticancer Drug Des 14, 517-538 (1999).
36. Kievit, E., Nyati, M. K., Ng, E., Stegman, L. D., Parsels, J., Ross, B. D., Rehemtulla, A. & Lawrence, T. S. Yeast cytosine deaminase improves radiosensitization and bystander effect by 5-fluorocytosine of human colorectal cancer xenografts. Cancer Res. 60, 6649-6655 (2000).
37. Dachs, G. U., Tupper, J. & Tozer, G. M. From bench to bedside for gene-directed enzyme prodrug therapy of cancer. Anticancer Drugs 16, 349-359 (2005).
38. Mahan, S. D., Ireton, G. C., Knoeber, C., Stoddard, B. L. & Black, M. E. Random mutagenesis and selection of *Escherichia coli* cytosine deaminase for cancer gene therapy. Protein Eng Des Sel 17, 625-633 (2004).
39. Mahan, S. D., Ireton, G. C., Stoddard, B. L. & Black, M. E. Alanine-scanning mutagenesis reveals a cytosine deaminase mutant with altered substrate preference. Biochemistry 43, 8957-8964 (2004).
40. Kievit, E., Bershad, E., Ng, E., Sethna, P., Dev, I., Lawrence, T. S. & Rehemtulla, A. Superiority of yeast over bacterial cytosine deaminase for enzyme/prodrug gene therapy in colon cancer xenografts. Cancer Res 59, 1417-1421 (1999).
41. Korkegian, A., Black, M. E., Baker, D. & Stoddard, B. L. Computational thermostabilization of an enzyme. Science. 308, 857-860 (2005).
42. Stolworthy, T. S., Korkegian, A. M., Willmon, C. L., Ardiani, A., Cundiff, J., Stoddard, B. L. & Black, M. E. Yeast cytosine deaminase mutants with increased thermostability impart sensitivity to 5-fluorocytosine. J Mol Biol 377, 854-869 (2008).
43. Semenza, G. L. Hypoxia and cancer. Cancer Metastasis Rev 26, 223-224 (2007).
44. Liao D, C. C., Seagroves T N, Johnson R S. Hypoxia-inducible factor-1 alpha is a key regulator of metastasis in a transgenic model of cancer initiation and progression. Cancer Research 67, 563-572 (2007).
45. Semenza, G. HIF-1 and tumor progression: pathophysiology and therapeutics. Trends in Molecular Medicine. 8, s62-s67 (2002).
46. Hirota, K. a. S., GL. Regulation and angiogenesis by hypoxia-inducible factor-1. Critical Reviews of Oncology and Hematology 59, 15-26 (2006).
47. Wang G L, J. B., Rue E A, Semenza G L. Hypoxia-inducible factor 1 is a basic-helix-loop-helix-PAS heterodimer regulated by cellular 02 tension. Proceedings of the National Academy of Science USA. 92, 5510-5514 (1995).
48. Wang G L, S. G. Purification and characterization of hypoxia-inducible factor 1. Journal of Biological Chemistry. 270, 1230-1237 (1995).
49. Semenza, G. L. Life with oxygen. Science, 318, 62-64 (2007).
50. Huang L E, G. J., Schau M, Bunn H F. Regulation of hypoxia-inducible factor 1 alpha is mediated by an $O_2$-dependent degradation domain via the ubiquitin-proteasome pathway. Proceedings of the National Academy of Science USA 95, 7987-7992 (1998).
51. Kallio P J, W. W., O'Brien S, Makino Y, Poellinger L. Regulation of the hypoxia-inducible transcription factor 1 alpha by the ubiquitin-proteasome pathway. Journal of Biological Chemistry 274, 6519-6525 (1999).
52. Berra E, B. E., Ginouves A, Volmat V, Roux D, Pouyssagur J. HIF prolyl-hydroxylase 2 is the key oxygen sensor setting low steady-state levels of HIF-1 alpha in normoxia. EMBO Journal 22, 4082-4090 (2003).

53. Hirota K, S. G. Regulation of hypoxia-inducible factor 1 by prolyl and asparaginyl hydroxylases. Biochemical and Biophysical Research Communications 338, 610-616 (2005).
54. Yu A Y, F. M., Shimoda L A, Wiener C M, Stenmark K, and Semenza, G L. Temporal, spatial, and oxygen-regulated expression of hypoxia-inducible factor-1 in the lung. American Journal of Physiology—Lung Cellular and Molecular Physiology 275, L818-L826 (1998).
55. Semenza, G. Hydroxylation of HIF-1: oxygen sensing at the molecular level. Physiology (Bethesda) 19, 176-182 (2004).
56. Lando, D., Peet, D. J., Gorman, J. J., Whelan, D. A., Whitelaw, M. L. & Bruick, R. K. F1H-1 is an asparaginyl hydroxylase enzyme that regulates the transcriptional activity of hypoxia-inducible factor. Genes Dev 16, 1466-1471 (2002).
57. Tomita M, S. G., Michiels C, Matsuda T, Uchihara J N, Okudaira T, Tanaka Y, Taira N, Ohshiro K, Mori N. Activation of hypoxia-inducible factor 1 in human T-cell leukemia virus type 1-infected cell lines and primary adult T-cell leukemia cells. The Biochemical Journal 406, 317-323 (2007).
58. Dang C V, S. G. Oncogenic alterations of metabolism. Trends in Biochemical Science 24, 68-72 (1999).
59. Semenza, G. Targeting HIF-1 for Cancer Therapy. Nature Reviews. Cancer 3, 721-732 (2003).
60. Mabjeesh N J, a. A. S. Hypoxia-inducible factor (REF) in human tumorigenesis. Histology and Histopathology 22, 559-572 (2007).
61. Semenza, G. L. Evaluation of HIF-1 inhibitors as anticancer agents. Drug Discov Today 12, 853-859 (2007).
62. Freedman, S. J., Sun, Z. Y., Poy, F., Kung, A. L., Livingston, D. M., Wagner, G. & Eck, M. J. Structural basis for recruitment of CBP/p300 by hypoxia-inducible factor-1 alpha. Proc Natl Acad Sci USA 99, 5367-5372 (2002).
63. Dames, S. A., Martinez-Yamout, M., De Guzman, R. N., Dyson, H. J. & Wright, P. E. Structural basis for Hif-1 alpha/CBP recognition in the cellular hypoxic response. Proc Natl Acad Sci USA 99, 5271-5276 (2002).
64. Kung, A. L., Zabludoff, S. D., France, D. S., Freedman, S. J., Tanner, E. A., Vieira, A., Cornell-Kennon, S., Lee, J., Wang, B., Wang, J., Memmert, K., Naegeli, H. U., Petersen, F., Eck, M. J., Bair, K. W., Wood, A. W. & Livingston, D. M. Small molecule blockade of transcriptional coactivation of the hypoxia-inducible factor pathway. Cancer Cell 6, 33-43 (2004).
65. Freedman, S. J., Sun, Z. Y., Kung, A. L., France, D. S., Wagner, G. & Eck, M. J. Structural basis for negative regulation of hypoxia-inducible factor-1alpha by CITED2. Nat Struct Biol 10, 504-512 (2003).
66. Dial, R., Sun, Z. Y. & Freedman, S. J. Three conformational states of the p300 CH1 domain define its functional properties. Biochemistry 42, 9937-9945 (2003).
67. Teufel, D. P., Freund, S. M., Bycroft, M. & Fersht, A. R. Four domains of p300 each bind tightly to a sequence spanning both transactivation subdomains of p53. Proc Nall Acad Sci USA 104, 7009-7014 (2007).
68. Ostermeier, M. & Benkovic, S. J. Evolution of protein function by domain swapping. Adv.Protein Chem. 55, 29-77 (2000).
69. Apic, G., Gough, J. & Teichmann, S. A. Domain combinations in archaeal, eubacterial and eukaryotic proteomes. J Mol Biol 310, 311-325 (2001).
70. Schlunegger, M. P., Bennett, M. J. & Eisenberg, D. Oligomer formation by 3D domain swapping: a model for protein assembly and misassembly. Adv.Protein Chem. 50, 61-122 (1997).
71. Berrondo, M., Ostermeier, M. & Gray, J. J. Structure prediction of domain insertion proteins from structures of individual domains. Structure. 16, 513-527 (2008).
72. Marvin, J. S. & Helling a, H. W Manipulation of ligand binding affinity by exploitation of conformational coupling. Nat Struct Biol 8, 795-798 (2001).
73. Millet, O., Hudson, R. P. & Kay, L. E. The energetic cost of domain reorientation in maltose-binding protein as studied by NMR and fluorescence spectroscopy. Proc Natl Acad Sci USA. 100, 12700-12705 (2003).
74. Ireton, G. C., McDermott, G., Black, M. E. & Stoddard, B. L. The structure of *Escherichia coli* cytosine deaminase. J Mol Biol 315, 687-697 (2002).
75. Ko, T. P., Lin, J. J., Hu, C. Y., Hsu, Y. H., Wang, A. H. & Liaw, S. H. Crystal structure of yeast cytosine deaminase. Insights into enzyme mechanism and evolution. J Biol. Chem. 278, 19111-19117 (2003).
76. Kohn, J. E. & Plaxco, K. W. Engineering a signal transduction mechanism for protein-based biosensors. Proc Natl Acad Sci USA 102, 10841-10845 (2005).
77. West, T. P. & O'Donovan, G. A. Repression of cytosine deaminase by pyrimidines in *Salmonella typhimurium*. J Bacteriol 149, 1171-1174 (1982).
78. Yao, L., Li, Y., Wu, Y., Liu, A. & Yan, H. Product release is rate-limiting in the activation of the prodrug 5-fluorocytosine by yeast cytosine deaminase. Biochemistry 44, 5940-5947 (2005).
79. Murai, M., Toyota, M., Suzuki, H., Satoh, A., Sasaki, Y., Akino, K., Ueno, M., Takahashi, F., Kusano, M., Mita, H., Yanagihara, K., Endo, T., Hinoda, Y., Tokino, T. & Imai, K. Aberrant methylation and silencing of the BNIP3 gene in colorectal and gastric cancer. Clth Cancer Res 11, 1021-1027 (2005).
80. Zhong, H., Agani, F., Baccala, A. A., Laughner, E., Rioseco-Camacho, N., Isaacs, W. B., Simons, J. W. & Semenza, G. L. Increased expression of hypoxia inducible factor-1alpha in rat and human prostate cancer. Cancer Res. 58, 5280-5284 (1998).
81. Mabjeesh, N.J., Post, D. E., Willard, M. T., Kaur, B., Van Meir, E. G., Simons, J. W. & Zhong, H. Geldanamycin induces degradation of hypoxia-inducible factor 1 alpha protein via the proteosome pathway in prostate cancer cells. Cancer Res. 62, 2478-2482 (2002).
82. Lee, M., Hwang, J. T., Lee, H. J., Jung, S, N., Kang, I., Chi, S. G., Kim, S. S. & Ha, J. AMP-activated protein kinase activity is critical for hypoxia-inducible factor-1 transcriptional activity and its target gene expression under hypoxic conditions in DU145 cells. J Biol Chem. 278, 39653-39661 (2003).
83. Kim, J. W., Gao, P., Liu, Y. C., Semenza, G. L. & Dang, C. V. Hypoxia-inducible factor 1 and dysregulated c-Myc cooperatively induce vascular endothelial growth factor and metabolic switches hexokinase 2 and pyruvate dehydrogenase kinase 1. Mol Cell Biol 27, 7381-7393 (2007).
84. Kim, J. W. & Dang, C. V. Cancer's molecular sweet tooth and the Watburg effect. Cancer Res 66, 8927-8930 (2006).
85. Parker, A. R., Leonard, C. P., Hua, L., Francis, R. O., Dhara, S., Maitra, A. & Eshleman, J. R. A subgroup of microsatellite stable colorectal cancers has elevated mutation rates and different responses to alkylating and oxidising agents. Br J Cancer 90, 1666-1671 (2004).
86. Wang, C.Y., Eshleman, J. R., Willson, J. K. & Markowitz, S. Both transforming growth factor-beta and substrate release are inducers of apoptosis in a human colon adenoma cell line. Cancer Res 55, 5101-5105 (1995).
87. Drake, R. R., Pitlyk, K., McMasters, R. A., Mercer, K. E., Young, H. & Moyer, M. P. Connexin-independent ganciclovir-mediated killing conferred on bystander effect-resistant cell lines by a herpes simplex virus-thymidine kinase-expressing colon cell line. Mol Ther 2, 515-523 (2000).
88. Polak-Charcon, S., Shoham, J. & Ben-Shaul, Y. Tight junctions in epithelial cells of human fetal hindgut, normal colon, and colon adenocarcinoma. J Natl Cancer Inst 65, 53-62 (1980).
89. Freedman, S. J., Sun, Z. Y., Poy, F., Kung, A. L., Livingston, D. M., Wagner, G., et al. (2002). Structural basis for recruitment of CBP/p300 by hypoxia-inducible factor-1 alpha. Proceedings of the National Academy of Sciences of the United States of America, 99(8), 5367-72.
90. Mabjeesh, N. J., & Amir, S. (2007). Hypoxia-Inducible factor (HIF) in human tumorigenesis. Histology and Histopathology, 22(5), 559-72.
91. Guntas, G., Mitchell, S. F., & Ostermeier, M. (2004). A molecular switch created by in vitro recombination of non-homologous genes. Chemistry & Biology, 11(11), 1483-7.
92. Korkegian, A., Black, M. E., Baker, D., & Stoddard, B. L. (2005). Computational thermostabilization of an enzyme. Science, 308(5723), 857-60.

What is claimed is:

1. A polypeptide encoding a molecular switch comprising a cytosine deaminase and a CH1 domain from p300, comprising the amino acid sequence of SEQ ID NO: 1.

2. A polypeptide encoding a molecular switch comprising a cytosine deaminase and a CH1 domain from p300, comprising the amino acid sequence of SEQ ID NO: 2.

3. A molecular switch for converting a prodrug into a toxin, comprising a cytosine deaminase and a CH1 domain corresponding to the amino acid sequence of SEQ ID NO: 1.

4. A molecular switch for converting a prodrug into a toxin, comprising a cytosine deaminase and a CH1 domain corresponding to the amino acid sequence of SEQ ID NO: 2.

* * * * *

SEQUENCE LISTING

```
<160> NUMBER OF SEQ ID NOS: 14

<210> SEQ ID NO 1
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Val Thr Gly Gly Met Ala Ser Gly Asp Pro Glu Lys Arg Lys Leu
1               5                   10                  15

Ile Gln Gln Leu Val Leu Leu His Ala His Lys Cys Gln Arg
            20                  25                  30

Arg Glu Gln Ala Asn Gly Glu Val Arg Gln Cys Asn Leu Pro His Cys
        35                  40                  45

Arg Thr Met Lys Asn Val Leu Asn His Met Thr His Cys Gln Ser Gly
    50                  55                  60

Lys Ser Cys Gln Val Ala His Cys Ala Ser Ser Arg Gln Ile Ile Ser
65                  70                  75                  80

His Trp Lys Asn Cys Thr Arg His Asp Cys Pro Val Cys Leu Pro Leu
                85                  90                  95

Lys Asn Ala Gly Gly Ser Lys Trp Asp Gln Lys Gly Met Asp Ile Ala
            100                 105                 110

Tyr Glu Glu Ala Leu Leu Gly Tyr Lys Glu Gly Gly Val Pro Ile Gly
        115                 120                 125

Gly Cys Leu Ile Asn Asn Lys Asp Gly Ser Val Leu Gly Arg Gly His
    130                 135                 140

Asn Met Arg Phe Gln Lys Gly Ser Ala Thr Leu His Gly Glu Ile Ser
145                 150                 155                 160

Thr Leu Glu Asn Cys Gly Arg Leu Glu Gly Lys Val Tyr Lys Asp Thr
                165                 170                 175

Thr Leu Tyr Thr Thr Leu Ser Pro Cys Asp Met Cys Thr Gly Ala Ile
            180                 185                 190

Ile Met Tyr Gly Ile Pro Arg Cys Val Ile Gly Glu Asn Val Asn Phe
        195                 200                 205

Lys Ser Lys Gly Glu Lys Tyr Leu Gln Thr Arg Gly His Glu Val Val
    210                 215                 220

Val Val Asp Asp Glu Arg Cys Lys Lys Leu Met Lys Gln Phe Ile Asp
225                 230                 235                 240

Glu Arg Pro Gln Asp Trp Phe Glu Asp Ile Gly Glu
                245                 250
```

<210> SEQ ID NO 2
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Met Val Thr Gly Gly Met Ala Ser Asp Pro Glu Lys Arg Lys Leu Ile
1               5                   10                  15

Gln Gln Gln Leu Val Leu Leu His Ala His Lys Cys Gln Arg Arg
            20                  25                  30

Glu Gln Ala Asn Gly Glu Val Arg Gln Cys Asn Leu Pro His Cys Arg
        35                  40                  45

Thr Met Lys Asn Val Leu Asn His Met Thr His Cys Gln Ser Gly Lys
    50                  55                  60

Ser Cys Gln Val Ala His Cys Ala Ser Ser Arg Gln Ile Ile Ser His
65                  70                  75                  80

Trp Lys Asn Cys Thr Arg His Asp Cys Pro Val Cys Leu Pro Leu Lys
                85                  90                  95

Asn Ala Gly Gly Trp Asp Gln Lys Gly Met Asp Ile Ala Tyr Glu Glu
            100                 105                 110

Ala Leu Leu Gly Tyr Lys Glu Gly Val Pro Ile Gly Gly Cys Leu
        115                 120                 125

Ile Asn Asn Lys Asp Gly Ser Val Leu Gly Arg Gly His Asn Met Arg
130                 135                 140

Phe Gln Lys Gly Ser Ala Thr Leu His Gly Glu Ile Ser Thr Leu Glu
145                 150                 155                 160

Asn Cys Gly Arg Leu Glu Gly Lys Val Tyr Lys Asp Thr Thr Leu Tyr
                165                 170                 175

Thr Thr Leu Ser Pro Cys Asp Met Cys Thr Gly Ala Ile Ile Met Tyr
            180                 185                 190

Gly Ile Pro Arg Cys Val Ile Gly Glu Asn Val Asn Phe Lys Ser Lys
        195                 200                 205

Gly Glu Lys Tyr Leu Gln Thr Arg Gly His Glu Val Val Val Val Asp
    210                 215                 220

Asp Glu Arg Cys Lys Lys Leu Met Lys Gln Phe Ile Asp Glu Arg Pro
225                 230                 235                 240

Gln Asp Trp Phe Glu Asp Ile Gly Glu
                245

<210> SEQ ID NO 3
<211> LENGTH: 759
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
atggtgacag ggggaatggc aagcggcgat ccggaaaaac gtaaactgat ccagcagcag    60
ctggtgctgc tgctgcatgc tcacaaatgt cagcgtcgtg aacaggcaaa cggcgaagta   120
cgtcagtgca acctgccgca ctgccgtaca atgaaaaatg tactgaacca catgacccac   180
tgccagagcg gtaaaagctg ccaggtagct cactgcgcat cttctcgcca gattatctct   240
cactggaaaa actgcacccg tcacgattgc ccggtttgct tgccgctcaa gaacgctggt   300

-continued

```
ggctcgaagt gggatcagaa gggtatggac attgcctatg aggaggcgct cttaggttac      360
aaagagggtg gtgttcctat tggcggatgt cttatcaata caaagacgg aagtgttctc       420
ggtcgtggtc acaacatgag atttcaaaag ggatccgcca cactacatgg tgagatctcc      480
actttggaaa actgtgggag attagagggc aaagtgtaca agataccac tttgtatacg       540
acgctgtctc catgcgacat gtgtacaggt gccatcatca tgtatggtat tccacgctgt      600
gttatcggtg agaacgttaa tttcaaaagt aagggcgaga atatttaca aactagaggt       660
cacgaggttg ttgttgttga cgatgagagg tgtaaaaagc tcatgaaaca atttatcgat      720
gaaagacctc aggattggtt tgaagatatt ggtgagtag                             759
```

<210> SEQ ID NO 4
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atggtgacag ggggaatggc aagcgatccg gaaaaacgta actgatcca gcagcagctg       60
gtgctgctgc tgcatgctca caaatgtcag cgtcgtgaac aggcaaacgg cgaagtacgt      120
cagtgcaacc tgccgcactg ccgtacaatg aaaaatgtac tgaaccacat gacccactgc      180
cagagcggta aaagctgcca ggtagctcac tgcgcatctt ctcgccagat tatctctcac      240
tggaaaaact gcacccgtca cgattgcccg gtttgcttgc cgctcaagaa cgctggtggc      300
tgggatcaga agggtatgga cattgcctat gaggaggcgc tcttaggtta caaagagggt      360
ggtgttccta ttggcggatg tcttatcaat acaaagacg gaagtgttct cggtcgtggt      420
cacaacatga gatttcaaaa gggatccgcc acactacatg gtgagatctc cactttggaa      480
aactgtggga gattagaggg caaagtgtac aagatacca cttttgtatac gacgctgtct      540
ccatgcgaca tgtgtacagg tgccatcatc atgtatggta ttccacgctg tgttatcggt      600
gagaacgtta atttcaaaag taagggcgag aatatttac aaactagagg tcacgaggtt      660
gttgttgttg acgatgagag gtgtaaaaag ctcatgaaac aatttatcga tgaaagacct      720
caggattggt ttgaagatat tggtgagtag                                       750
```

<210> SEQ ID NO 5
<211> LENGTH: 427
<212> TYPE: PRT
<213> ORGANISM: Escherichia coli

<400> SEQUENCE: 5

```
Met Ser Asn Asn Ala Leu Gln Thr Ile Ile Asn Ala Arg Leu Pro Gly
1               5                   10                  15
Glu Glu Gly Leu Trp Gln Ile His Leu Gln Asp Gly Lys Ile Ser Ala
            20                  25                  30
Ile Asp Ala Gln Ser Gly Val Met Pro Ile Thr Glu Asn Ser Leu Asp
        35                  40                  45
Ala Glu Gln Gly Leu Val Ile Pro Pro Phe Val Glu Pro His Ile His
    50                  55                  60
Leu Asp Thr Thr Gln Thr Ala Gly Gln Pro Asn Trp Asn Gln Ser Gly
65                  70                  75                  80
Thr Leu Phe Glu Gly Ile Glu Arg Trp Ala Glu Arg Lys Ala Leu Leu
                85                  90                  95
```

Thr His Asp Asp Val Lys Gln Arg Ala Trp Gln Thr Leu Lys Trp Gln
                100                 105                 110

Ile Ala Asn Gly Ile Gln His Val Arg Thr His Val Asp Val Ser Asp
            115                 120                 125

Ala Thr Leu Thr Ala Leu Lys Ala Met Leu Glu Val Lys Gln Glu Val
130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
    370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425

<210> SEQ ID NO 6
<211> LENGTH: 158
<212> TYPE: PRT
<213> ORGANISM: Saccharomyces cerevisiae

<400> SEQUENCE: 6

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg

```
            35                  40                  45
Gly His Asn Met Arg Phe Gln Lys Gly Ser Ala Thr Leu His Gly Glu
        50                  55                  60

Ile Ser Thr Leu Glu Asn Cys Gly Arg Leu Glu Gly Lys Val Tyr Lys
 65                  70                  75                  80

Asp Thr Thr Leu Tyr Thr Thr Leu Ser Pro Cys Asp Met Cys Thr Gly
                     85                  90                  95

Ala Ile Ile Met Tyr Gly Ile Pro Arg Cys Val Val Gly Glu Asn Val
                100                 105                 110

Asn Phe Lys Ser Lys Gly Glu Lys Tyr Leu Gln Thr Arg Gly His Glu
            115                 120                 125

Val Val Val Val Asp Asp Glu Arg Cys Lys Lys Ile Met Lys Gln Phe
        130                 135                 140

Ile Asp Glu Arg Pro Gln Asp Trp Phe Glu Asp Ile Gly Glu
145                 150                 155

<210> SEQ ID NO 7
<211> LENGTH: 4082
<212> TYPE: DNA
<213> ORGANISM: Homo sapiens

<400> SEQUENCE: 7
gcgcgcgccg gcctgggcag gcgagcgggc gcgctcccgc cccctctccc ctccccgcgc      60
gcccgagcgc gcctccgccc ttgcccgccc cctgacgctg cctcagctcc tcagtgcaca     120
gtgctgcctc gtctgagggg acaggaggat caccctcttc gtcgcttcgg ccagtgtgtc     180
gggctgggcc ctgacaagcc acctgaggag aggctcggag ccgggcccgg accccggcga     240
ttgccgcccg cttctctcta gtctcacgag gggtttcccg cctcgcaccc ccacctctgg     300
acttgccttt ccttctcttc tccgcgtgtg gagggagcca gcgcttaggc cggagcgagc     360 ctggggggccg cccgccgtga agacatcgcg gggaccgatt caccatggag ggcgccggcg     420
gcgcgaacga caagaaaaag ataagttctg aacgtcgaaa agaaaagtct cgagatgcag     480
ccagatctcg gcgaagtaaa gaatctgaag tttttatga gcttgctcat cagttgccac     540
ttccacataa tgtgagttcg catcttgata aggcctctgt gatgaggctt accatcagct     600
atttgcgtgt gaggaaactt ctggatgctg tgatttggga tattgaagat gacatgaaag     660
cacagatgaa ttgcttttat ttgaaagcct tggatggttt tgttatggtt ctcacagatg     720
atggtgacat gatttacatt tctgataatg tgaacaaata catgggatta actcagtttg     780
aactaactgg acacagtgtg tttgatttta ctcatccatg tgaccatgag gaatgagag     840 aaatgcttac acacagaaat ggccttgtga aaagggtaa agaacaaaac acacagcgaa     900
gcttttttct cagaatgaag tgtaccctaa ctagccgagg aagaactatg aacataaagt     960
ctgcaacatg gaaggtattg cactgcacag gccacattca cgtatatgat accaacagta    1020
accaacctca gtgtgggtat aagaaaccac ctatgacctg cttggtgctg atttgtgaac    1080
ccattcctca cccatcaaat attgaaattc ctttagatag caagactttc ctcagtcgac    1140
acagcctgga tatgaaattt tcttattgtg atgaaagaat taccgaattg atgggatatg    1200
agccagaaga actttaggc cgctcaattt atgaatatta tcatgctttg gactctgatc    1260
atctgaccaa aactcatcat gatatgttta ctaaaggaca agtcaccaca ggacagtaca    1320
ggatgcttgc caaagaggt ggatatgtct gggttgaaac tcaagcaact gtcatatata    1380
acaccaagaa ttctcaacca cagtgcattg tatgtgtgaa ttacgttgtg agtggtatta    1440
```

```
ttcagcacga cttgattttc tcccttcaac aaacagaatg tgtccttaaa ccggttgaat    1500
cttcagatat gaaaatgact cagctattca ccaaagttga atcagaagat acaagtagcc    1560
tctttgacaa acttaagaag gaacctgatg ctttaacttt gctggcccca gccgctggag    1620
acacaatcat atctttagat tttggcagca acgacacaga aactgatgac cagcaacttg    1680
aggaagtacc attatataat gatgtaatgc tcccctcacc caacgaaaaa ttacagaata    1740
taaatttggc aatgtctcca ttacccaccg ctgaaacgcc aaagccactt cgaagtagtg    1800
ctgaccctgc actcaatcaa gaagttgcat taaaattaga accaaatcca gagtcactgg    1860
aactttcttt taccatgccc cagattcagg atcagacacc tagtccttcc gatggaagca    1920
ctagacaaag ttcacctgag cctaatagtc ccagtgaata ttgttttat gtggatagtg    1980 atatggtcaa tgaattcaag ttggaattgg tagaaaaact ttttgctgaa gacacagaag    2040
caaagaaccc attttctact caggacacag atttagactt ggagatgtta gctccctata    2100
tcccaatgga tgatgacttc cagttacgtt ccttcgatca gttgtcacca ttagaaagca    2160
gttccgcaag ccctgaaagc gcaagtcctc aaagcacagt tacagtattc cagcagactc    2220
aaatacaaga acctactgct aatgccacca ctaccactgc caccactgat gaattaaaaa    2280
cagtgacaaa agaccgtatg gaagacatta aaatattgat tgcatctcca tctcctaccc    2340
acatacataa agaaactact agtgccacat catcaccata tagagatact caaagtcgga    2400
cagcctcacc aaacagagca ggaaaaggag tcatagaaca gacagaaaaa tctcatccaa    2460
gaagccctaa cgtgttatct gtcgctttga gtcaaagaac tacagttcct gaggaagaac    2520
taaatccaaa gatactagct ttgcagaatg ctcagagaaa gcgaaaaatg gaacatgatg    2580
gttcactttt tcaagcagta ggaattggaa cattattaca gcagccagac gatcatgcag    2640
ctactacatc actttcttgg aaacgtgtaa aaggatgcaa atctagtgaa cagaatggaa    2700
tggagcaaaa gacaattatt ttaataccct ctgatttagc atgtagactg ctggggcaat    2760
caatggatga aagtggatta ccacagctga ccagttatga ttgtgaagtt aatgctccta    2820
tacaaggcag cagaaaccta ctgcagggtg aagaattact cagagctttg gatcaagtta    2880
actgagcttt tcttaatttt cattcctttt tttggacact ggtggctcat tacctaaagc    2940
agtctattta tattttctac atctaatttt agaagcctgg ctacaatact gcacaaactt    3000
ggttagttca attttgatcc ccttctact taatttacat taatgctctt ttttagtatg    3060
ttctttaatg ctggatcaca gacagctcat tttctcagtt ttttggtatt taaaccattg    3120
cattgcagta gcatcatttt aaaaaatgca cctttttatt tatttatttt tggctaggga    3180
gtttatccct ttttcgaatt attttttaaga agatgccaat ataatttttg taagaaggca    3240
gtaacctttc atcatgatca taggcagttg aaaaattttt acccttttt tttcacattt    3300 tacataaata ataatgcttt gccagcagta cgtggtagcc acaattgcac aatatatttt    3360
cttaaaaaat accagcagtt actcatggaa tatattctgc gtttataaaa ctagttttta    3420
agaagaaatt ttttttggcc tatgaaattg ttaaacctgg aacatgacat tgttaatcat    3480
ataataatga ttcttaaatg ctgtatggtt tattatttaa atgggtaaag ccatttacat    3540
aatatagaaa gatatgcata tatctagaag gtatgtggca tttatttgga taaaattctc    3600
aattcagaga aatcatctga tgtttctata gtcactttgc cagctcaaaa gaaaacaata    3660
ccctatgtag ttgtggaagt ttatgctaat attgtgtaac tgatattaaa cctaaatgtt    3720
ctgcctaccc tgttggtata aagatatttt gagcagactg taaacaagaa aaaaaaaatc    3780
atgcattctt agcaaaattg cctagtatgt taatttgctc aaaatacaat gtttgatttt    3840
```

```
atgcactttg tcgctattaa catccttttt ttcatgtaga tttcaataat tgagtaattt    3900
tagaagcatt attttaggaa tatatagttg tcacagtaaa tatcttgttt tttctatgta    3960
cattgtacaa attttcatt ccttttgctc tttgtggttg gatctaacac taactgtatt     4020
gttttgttac atcaaataaa catcttctgt ggaccaggca aaaaaaaaaa aaaaaaaaa     4080 aa                                                                   4082
```

<210> SEQ ID NO 8
<211> LENGTH: 826
<212> TYPE: PRT
<213> ORGANISM: Homo sapiens

<400> SEQUENCE: 8

```
Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320
```

```
Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
```

```
                        740                 745                 750
Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
        770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ser Gly Gly Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Gly Gly Gly Gly Ser Gly Gly Gly
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ser Gly Gly Gly Gly Ser Gly Gly Gly Gly Ser Gly Gly Gly
1               5                   10                  15

<210> SEQ ID NO 13
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 13

Gly Ser Gly Gly
1

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5
```